United States Patent [19]
Toh

[11] Patent Number: 6,125,331
[45] Date of Patent: Sep. 26, 2000

[54] STRUCTURAL ALIGNMENT METHOD MAKING USE OF A DOUBLE DYNAMIC PROGRAMMING ALGORITHM

[75] Inventor: Hiroyuki Toh, Suita, Japan

[73] Assignee: Biomolecular Engineering Research Institute, Suita, Japan

[21] Appl. No.: 08/992,176

[22] Filed: Dec. 17, 1997

[30] Foreign Application Priority Data

Dec. 20, 1996 [JP] Japan ................................. 8-340727

[51] Int. Cl.⁷ ........................... G06F 19/00; G01N 31/00
[52] U.S. Cl. ................................................ 702/19; 702/27
[58] Field of Search .............................. 364/578; 702/19, 702/27

[56] References Cited

U.S. PATENT DOCUMENTS 5,436,850  7/1995  Eisenberg et al. ..................... 364/496
5,878,373  3/1999  Cohen et al. ........................... 702/22

*Primary Examiner*—Bennett Celsa
*Assistant Examiner*—Joseph W. Ricigliano
*Attorney, Agent, or Firm*—Oblon, Spivak, McClelland, Maier & Neustadt, P.C.

[57] ABSTRACT

There is disclosed a structural alignment method making use of a double dynamic programming algorithm. A distance cut-off approximation is performed, and then ΔN cut-off approximation is performed. An alignment is produced based on the results of the distance cut-off approximation and the ΔN cut-off approximation. Subsequently, an ε-suboptimal region defined by the obtained approximate solution is determined. Further, double dynamic programing alignment on the full structural environment is performed for residue pairs within the ε-suboptimal region. The structural alignment method is simpler than conventional methods and can shorten computational time while maintaining high accuracy.

20 Claims, 32 Drawing Sheets

STRUCTURE OF PROTEIN B

STRUCTURE OF PROTEIN A

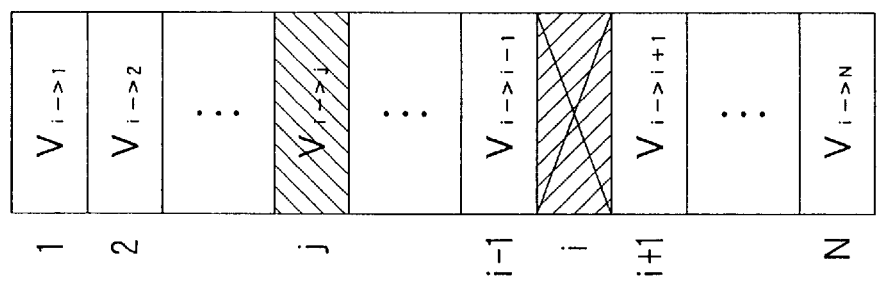
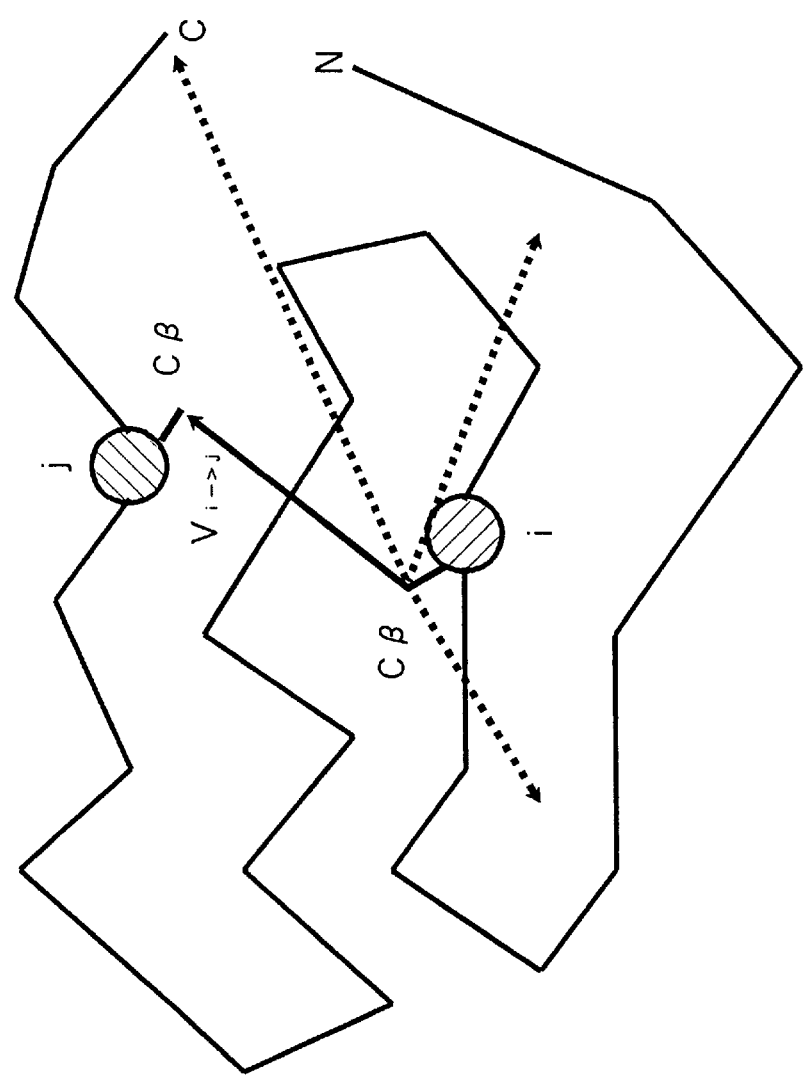
FIG. 4
PRIOR ART

FIG. 5 PRIOR ART
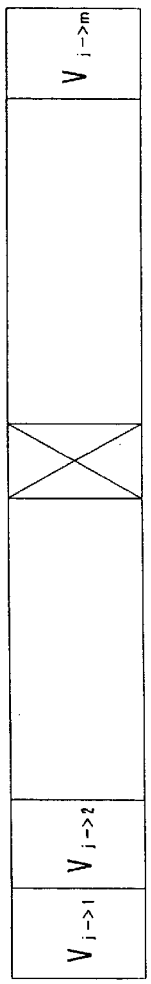
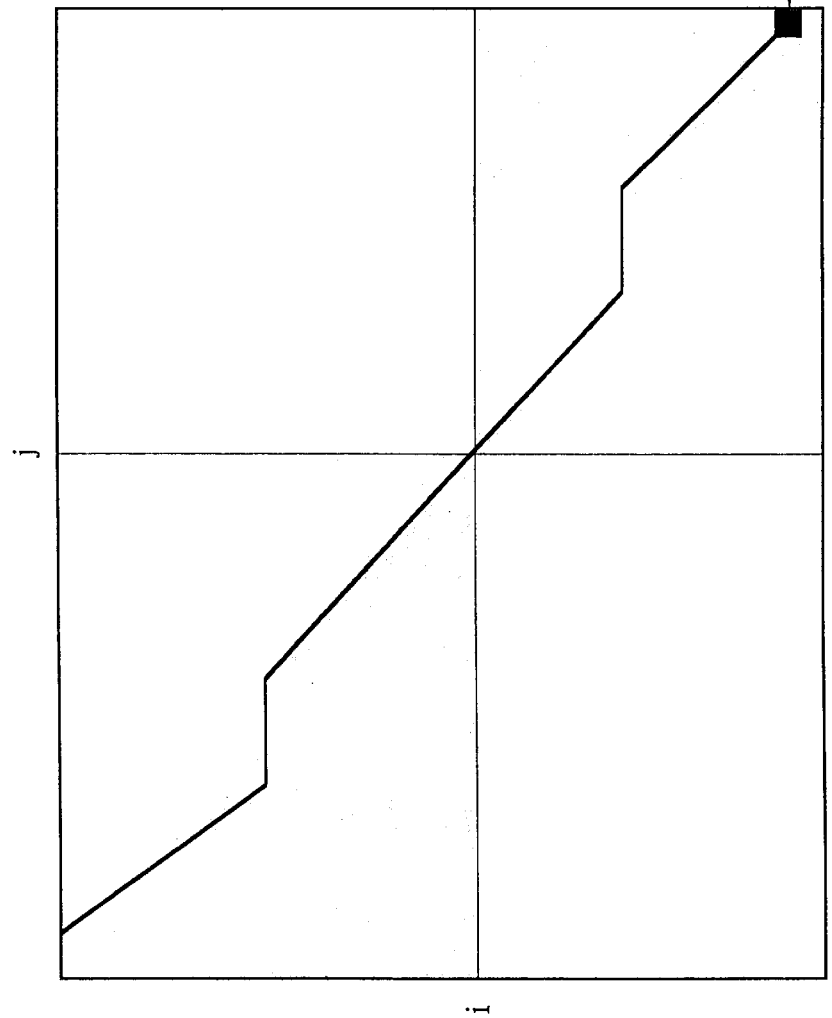
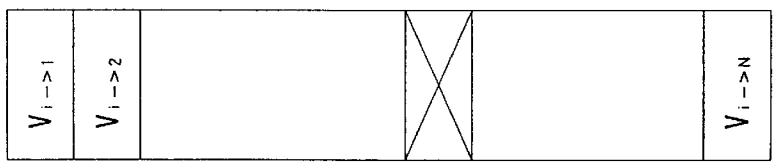
$$D(x,y) = \text{Max} \{s(x,y) + D(x-1, y-1), D(x-1, y) - \beta, D(x, y-1) - \beta\}$$
$$s(x,y) = \frac{a}{|V_{i \to x} - V_{j \to y}|^2 + b}$$

METHOD FOR REDUCING COMPUTATIONAL TIME PROPOSED BY TAYLOR AND ORENGO

FIG. 9
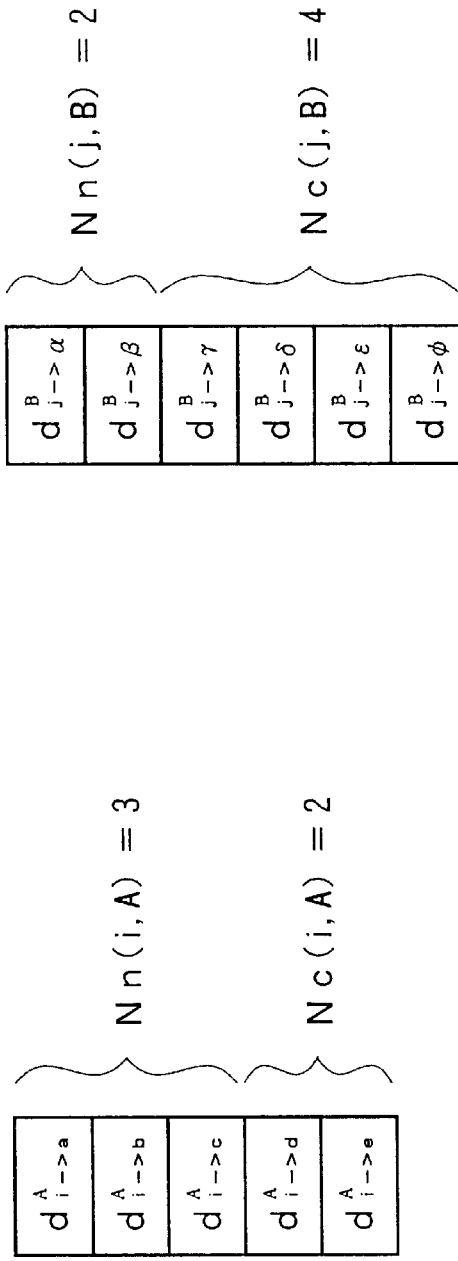
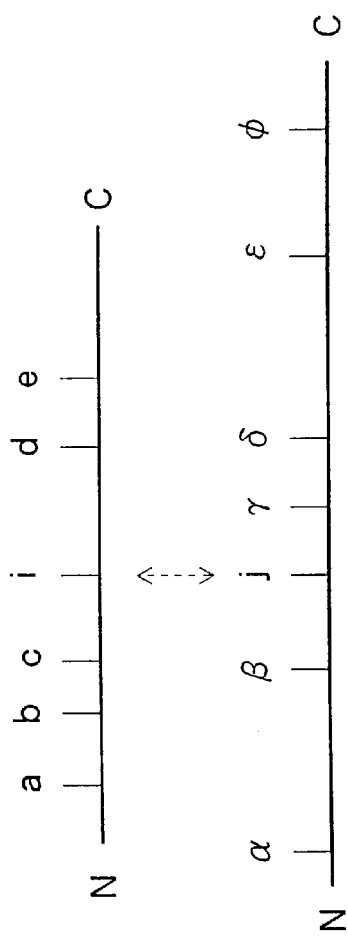

FIG. 22

| examined structures | | PDB identification code |
|---|---|---|
| CASE 1 (SEE FIG. 23) | β-PROTEIN<br>VARIABLE DOMAIN OF HUMAN IMMUNOGLOBULIN LIGHT CHAIN<br>VARIABLE DOMAIN OF HUMAN IMMUNOGLOBULIN HEAVY CHAIN | 7fab<br>7fab |
| CASE 2 (SEE FIG. 24) | β-PROTEIN<br>MURINE URINARY PROTEIN<br>RAT EPIDIDYMAL RETINOIC ACID-BINDING PROTEIN | 1mup<br>1epb |
| CASE 3 (SEE FIG. 25) | α-PROTEIN<br>SPERM WHALE MYOGLOBIN<br>YELLOW LUPIN LEGHEMOGLOBIN | 1mbc<br>1gdi |
| CASE 4 (SEE FIG. 26) | α-PROTEIN<br>SPERM WHALE MYOGLOBIN<br>CYANOBACTERIUM C-PHYCOCYANIN | 1mbc<br>1cpc |

(A)

```
         1.........+.........+.........+.........+.........+.........+
7fabl    ASVLTQPPSVS-GAPGQRVTISCTGSSSN-IGAGHNVKWYQQLPGTAPK---LL-----I
7fabh    AVQLEQS-GPGLVRPSQTLSLTCTVS-GTSFD-DYYWTWVRQPPGRGLEWIGYVFYTGTT
         •  ••oo  o   •o•  ooooo••  •  o    •       •  •••  o      o 61........+.........+.........+.........+.........+.........+
7fabl    -FH-NN-ARFSVSKSG--TSATLAITGLQAEDEADYYCQSYDRS-L-RVFGGGTKLTVLR
7fabh    LLDPSLRGRVTMLVNTSKNQFSLRLSSVTAADTAVYYCARNLIAGGIDVWGQGSLVTVSS
            o•  oo    o      o•  oooo  •  •  •  •••      o     ••o  •o  o••

121..
7fabl    --
7fabh    AS
```

(B)

```
         1.........+.........+.........+.........+.........+.........+
7fabl    ASVLTQPPSVSGAPGQRVTISCTGSSSNIGAGHNVKWYQQLPGTAPKLL---------IF
7fabh    AVQLEQSGPGLVRPSQTLSLTCTVS-GTSFDDYYWTWVRQPPGRGLEWIGYVFYTGTTLL
         •  •  •ooo   •o•  ooooo••  •  o    •  •••  o   o               o 61........+.........+.........+.........+.........+.........+
7fabl    -HNN-ARFSVSKSG--TSATLAITGLQAEDEADYYCQSYDRSL--RVFGGGTKLTVL--R
7fabh    DPSLRGRVTMLVNTSKNQFSLRLSSVTAADTAVYYCARNLIAGGIDVWGQGSLVTVSSAS
         o•  oo    o      o•  oooo  •  •  •  •••      o     ••o  •o  o••
```

```
         1.........+.........+.........+.........+.........+.........+
lmup     EEASSTGRNFNVEKINGEWHTIILASDKRE--KI-EDNGNFRLFLEQIHVLENSLVLKFH
lepb     ----V-K-DFDISKFLGFWYEIAFA-SKMGTPGLAHKEEKM-GAMV-VELKENLLALTTT
             o•oo •  • •   •   •       o   o    o  oo •• ••

61........+.........+.........+.........+.........+.........+
lmup     TVRDEECSELSMVADKTEKAGEYSVTY--DGFNTFTIPKTDYDNFLMAHLINEKDGETFQ
lepb     YYSEDHCVLEKVTATEGDGPAKFQVTRLSGKKEV-VVEATDYLTYAIIDITSLVAGAVHR
            oo •    o • oo oo o  ••      o    o  •••  oo  o      •

121.......+.........+.........+.........+.........+.........+
lmup     LMGLYGREP-DLSSDIKERFAQLCEEHGILRENIIDL--S-NAN-R-C---
lepb     TMKLYSRSLDDNGE-ALYNFRKITSDHGFSETDLYILKHDLTCVKVLQSAA
          • ••o•  • o    •  o  ••   oo  •
```

(D)

```
         1.........+.........+.........+.........+.........+.........+
lmup     EEASSTGRNFNVEKINGEWHTIILASDKREKIEDNGNFRLFLEQIHVLENSLVLKFHTVR
lepb     --V---K-DFDISKFLGFWYEIAFASKMGTPGLAHKEEKMGAMVVELKENLLALTTTYYS
             o•oo • •  • •  ••         o oo    o oo •• • •

61........+.........+.........+.........+.........+.........+
lmup     DEECSELSMVADKTEKAGEYSVTYD-GFNTFTIPKTDYDNFLMAHLINEKDGETFQLMGL
lepb     EDHCVLEKVTATEGDGPAKFQVTRLSGKKEVVVEATDYLTYAIIDITSLVAGAVHRTMKL
         oo •    o • oo oo o  ••   •    o  •••  oo  o       •    ••

121.......+.........+.........+.........+......
lmup     YGREPDLSSDIKERFAQLCEEHGILRENIIDL-S-N-ANRC-----
lepb     YSRSLDDNGEALYNFRKITSDHGFSETDLYILKHDLTCVKVLQSAA
         •••  •  oo    •   o  •••   oo  •        o
```

*FIG. 24A*

(E)    1.........+.........+.........+.........+.........+.........+ lmup   EEASSTGRNFNVEKINGEWHTIILASDKREKIEDN--GNFRLFLEQIHVLENSLVLKFHT
lepb   --V---K-DFDISKFLGFWYEIAFASKMGTPGLAHKEEK-MGAM-VVELKENLLALTTTY
       o·oo · ·· · ··                          o  oo ·· · ·

61.........+.........+.........+.........+.........+.........+ lmup   VRDEECSELSMVADKTEKAGEYSVTYD-GFNTFTIPKTDYDNFLMAHLINEKDGETFQLM
lepb   YSEDHCVLEKVTATEGDGPAKFQVTRLSGKKEVVVEATDYLTYAIIDITSLVAGAVHRTM
       oo ·    o · oo oo o ··   ·    o ··· oo  o       ·

121.........+.........+.........+.........+.........+.........+ lmup   GLYGREPDLSSDIKERFAQLCEEHGILRENIIDL-S-N-ANRC-----
lepb   KLYSRSLDDNGEALYNFRKITSDHGFSETDLYILKHDLTCVKVLQSAA
       ··o· ·  oo    ·  o  o ···  oo  ·       o

*FIG. 24B*

(F)   1 .........+.........+.........+.........+.........+.........+ lmbc   -VLSEGEWQLVLHVWAKVEADVAGHGDDILIRLFKSHPETLEKFDRFKHLKTEAEMKASE
lgdi   GALTESQAALVKSSWEEFNANIPKHTHRFFILVLEIAPAAKDLFSFLKGTS-E-VPQNNP
        ••○○  ••  •   ○•○○○ •○   • ○   • ○○•   •   •

61 .........+.........+.........+.........+.........+.........+ lmbc   DLKKHGVTVLTALGAILK-KK--GHHE-A-ELKPLAQSHATKHKIPIKYLEFISEAIIHV
lgdi   ELQAHAGKVFKLVYEAAIQLEVTGVVVTDATLKNLGSVHVS-KGVADAHFPVVKEAILKT
       ○•  ○•  ○    •        •• •○  • ○ ○ ○○     ○ •••○○

121 .........+.........+.........+.........+.........+.........+ lmbc   LHSRHP-GDFGADAQGAMNKALELFRKDIAAKYKELGYQG
lgdi   IKEVVGAKWSE-ELNSAWTIAYDELAIVIKKEM--D-DAA
       ○○  ○    ○ ○○•   •○   •          ○

(G)   1 .........+.........+.........+.........+.........+.........+ lmbc   -VLSEGEWQLVLHVWAKVEADVAGHGQDILIRLFKSHPETLEKFDRFKHLKTEAEMKASE
lgdi   GALTESQAALVKSSWEEFNANIPKHTHRFFILVLEIAPAAKDLFSFLKGTSEV--PQNNP
        ••○○  ••  •   ○•○○○ •○   • ○   • ○○•   •

61 .........+.........+.........+.........+.........+.........+ lmbc   DLKKHGVTVLTALGAILKK-K-GH-HEAE--LKPLAQSHATKHKIPIKYLEFISEAIIHV
lgdi   ELQAHAGKVFKLVYEAAIQLEVTGVVVTDATLKNLGSVH-VSKGVADAHFPVVKEAILKT
       ○•  ○•  ○    •         ○○  ••○•   ○ ○○     ○ •••○○

121 .........+.........+.........+.........+.........+.........+ lmbc   LHSRHPGDFGADAQGAMNKALELFRKDIAAKYKELGYQG
lgdi   IKEVVGAKWSEELNSAWTIAYDELAIVIKKEMDDA-A--
       ○○  ○○ ○○ ○ ○○○  •○   •         ○

FIG. 25

(H)
```
         1.........+.........+.........+.........+.........+.........+
lcpc     MKTPLTEAVAAADSQGRFLSSTEIQTAFGRFRQASASLAAAKALTEKASSLASGAANA-V
lmbc     -VL--S-EG--------------------E--WQ-LVLHVWAKVEADVAGHGQDIL-IRL 61........+.........+.........+.........+.........+.........+
lcpc     YSKFPYTTSQNGPN-FASTQTGKDKC--VR-DIGYYLRMVTYCLV-VGG-T-GPLDDYLI
lmbc     FKSHPETLEKFDRFKHLKTEAEMKASEDLKKHGVTVLTALGAILKKK-GHHEAELKP-LA 121........+.........+.........+.........+.........+.........+
lcpc     GGIAEINRTFD--LSPSWYVEALK-YIKANH--GLSGDPAVEAN-SY--ID-YAINAL--
lmbc     QSHATKH-KIPIKY-LEFISEAIIHVLHSRHPGDFGADAQGAMNKALELFRKDIAAKYKE 181.....
lcpc     ---S-
lmbc     LGYQG
```

(I)
```
         1.........+.........+.........+.........+.........+.........+
lcpc     MKTPLTEAVAAADSQGRFLSSTEIQTAFGRFRQASASLAAAKALTEKASSLASGAANAVY
lmbc     VLSE--G--------------------E--WD-LVLHVWAKVEADVAGHGQDILIRLF 61........+.........+.........+.........+.........+.........+
lcpc     SKFPYTTSQ-NGPNFAST-QTG--KDKCVRDIGYYLRMVTYCLVVGG-TGPLDDYLIGGI
lmbc     KSHPETLEKFDRFKHLKTEAEMKASEDLKKHGVTVLTALGAILKKKGHHEAELKPLAQSH 121........+.........+.........+.........+.........+.........+
lcpc     AEINRTFDLSPSWYVEAL-KYIKANHG--LSGDPAVEANSYIDYAI----N-AL--S----
lmbc     ATKHKIPIKYLEFISEAIIHVLHSRHPGDFGADAQGAMNKALELFRKDIAAKYKELGYQG
```

| | ROUGH ALIGNMENT CUT-OFF DISTANCE=12.0Å ΔN=10 | | | ALIGNMENT IN FSE | |
|---|---|---|---|---|---|
| | RMSD | CPU time | identity | RMSD | CPU time |
| 7fab variable domains heavy vs light | 2.353 Å | 4.5 sec | 78.7 % | 2.163 Å | 184.2 sec |
| 1mup vs 1epb | 2.503 Å | 9.8 sec | 73.1 % | 2.530 Å | 770.9 sec |
| 1mbc vs 1gdi | 1.979 Å | 9.4 sec | 88.1 % | 1.869 Å | 659.0 sec |
| 1mbc vs 1cpc | 4.424 Å | 9.6 sec | 63.2 % | 4.100 Å | 737.9 sec |

F I G. 28

| | TWO-STEP ALIGNMENT CUT-OFF DISTANCE=12.0Å ΔN=10, ε=2.0σ | | | ALIGNMENT IN FSE | |
|---|---|---|---|---|---|
| | RMSD | CPU time | identity | RMSD | CPU time |
| 7fab variable domains heavy vs light | 2.163 Å | 15.2 sec | 100.0 % | 2.163 Å | 184.2 sec |
| 1mup vs 1epb | 2.215 Å | 35.9 sec | 94.0 % | 2.530 Å | 770.9 sec |
| 1mbc vs 1gdi | 1.869 Å | 31.2 sec | 100.0 % | 1.869 Å | 659.0 sec |
| 1mbc vs 1cpc | 4.100 Å | 46.6 sec | 100.0 % | 4.100 Å | 737.9 sec |

F I G. 29
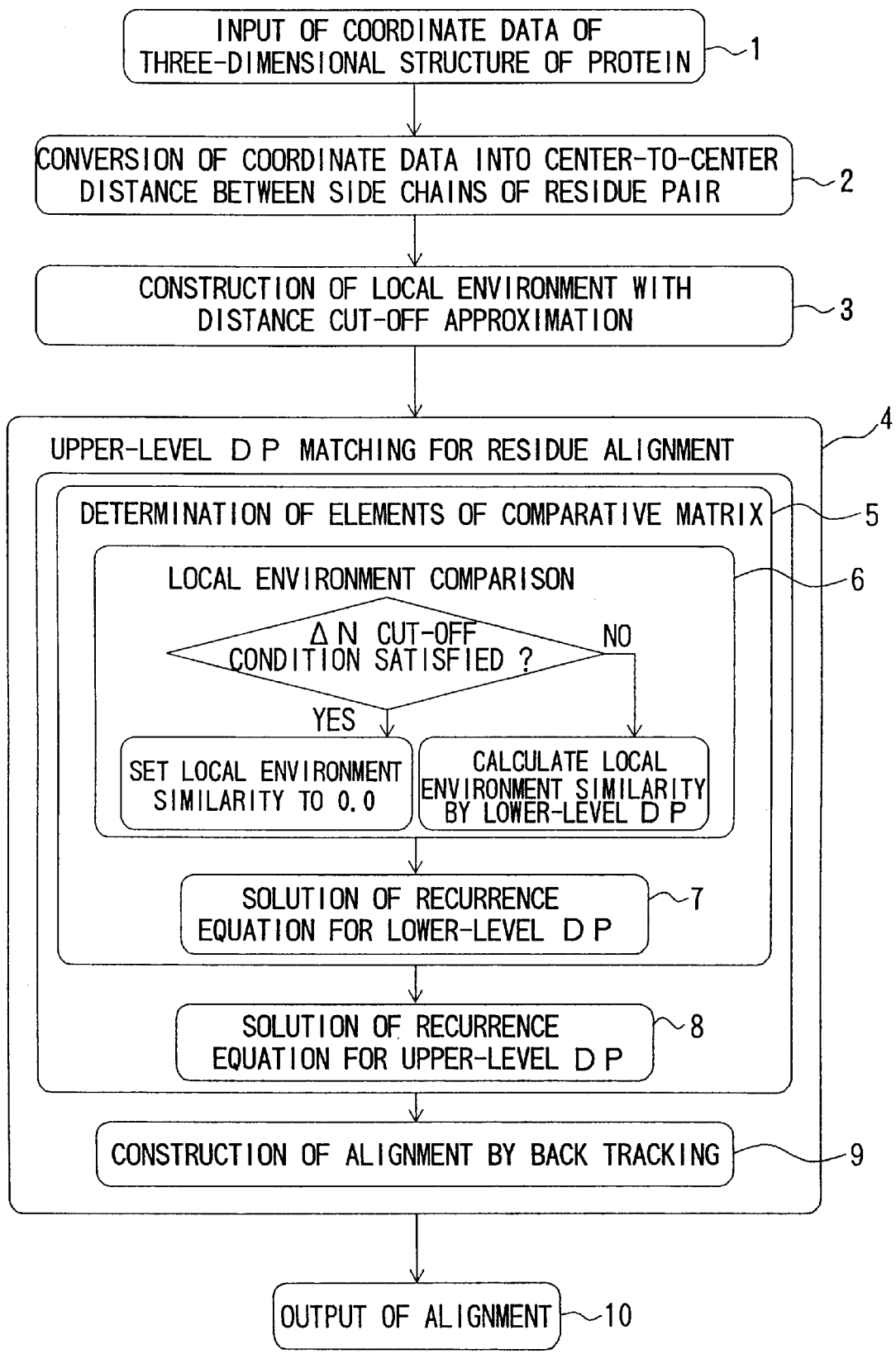

SEQUENCE LISTING

<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:peptide

<400> SEQUENCE: 1

Ala Cys Glu Leu Ser Ile Ser Arg Asn Tyr Asp Thr Ile Pro Asp
 1               5                  10                  15

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence:peptide

<400> SEQUENCE: 2

Val Ala Ser Gln Ile Gly Trp Asp Glu Asp Ile His Leu Glu Pro Ile
 1               5                  10                  15

Gly Glu Ser

<210> SEQ ID NO 3
<211> LENGTH: 103
<212> TYPE: PRT
<213> ORGANISM: Artificial Sequence
<220> FEATURE:
<223> OTHER INFORMATION: Description of Artificial Sequence:
      beta-protein (7fabl)

<400> SEQUENCE: 3

Ala Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

His Asn Val Lys Trp Tyr Gln Gln Leu Pro Gly Thr Ala Pro Lys Leu
            35                  40                  45

Leu Ile Phe His Asn Asn Ala Arg Phe Ser Val Ser Lys Ser Gly Thr
        50                  55                  60

Ser Ala Thr Leu Ala Ile Thr Gly Leu Gln Ala Glu Asp Glu Ala Asp
 65                  70                  75                  80

Tyr Tyr Cys Gln Ser Tyr Asp Arg Ser Leu Arg Val Phe Gly Gly Gly
                85                  90                  95

Thr Lys Leu Thr Val Leu Arg
            100

<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence:
      beta-protein (7fabh)

<400> SEQUENCE: 4

Ala Val Gln Leu Glu Gln Ser Gly Pro Gly Leu Val Arg Pro Ser Gln
1               5                   10                  15

Thr Leu Ser Leu Thr Cys Thr Val Ser Gly Thr Ser Phe Asp Asp Tyr
            20                  25                  30

Tyr Trp Thr Trp Val Arg Gln Pro Pro Gly Arg Gly Leu Glu Trp Ile
            35                  40                  45

Gly Tyr Val Phe Tyr Thr Gly Thr Thr Leu Leu Asp Pro Ser Leu Arg
        50                  55                  60

Gly Arg Val Thr Met Leu Val Asn Thr Ser Lys Asn Gln Phe Ser Leu
65                  70                  75                  80

Arg Leu Ser Ser Val Thr Ala Ala Asp Thr Ala Ala Asp Thr Ala Val
                85                  90                  95

Tyr Tyr Cys Ala Arg Asn Leu Ile Ala Gly Gly Ile Asp Val Trp Gly
            100                 105                 110

Gln Gly Ser Leu Val Thr Val Ser Ser Ala Ser
            115                 120

<210> SEQ ID NO 5
<211> LENGTH: 157
<212> TYPE: PRT
<213> ORGANISM: Artificial Sequence
<220> FEATURE:
<223> OTHER INFORMATION: Description of Artificial Sequence:
      beta-protein (1mup)

<400> SEQUENCE: 5

Glu Glu Ala Ser Ser Thr Gly Arg Asn Phe Asn Val Glu Lys Ile Asn
1               5                   10                  15

Gly Glu Trp His Thr Ile Ile Leu Ala Ser Asp Lys Arg Glu Lys Ile
            20                  25                  30

Glu Asp Asn Gly Asn Phe Arg Leu Phe Leu Glu Gln Ile His Val Leu
            35                  40                  45

Glu Asn Ser Leu Val Leu Lys Phe His Thr Val Arg Asp Glu Glu Cys
        50                  55                  60

Ser Glu Leu Ser Met Val Ala Asp Lys Thr Glu Lys Ala Gly Glu Tyr
65                  70                  75                  80

Ser Val Thr Tyr Asp Gly Phe Asn Thr Phe Thr Ile Pro Lys Thr Asp
                85                  90                  95

Tyr Asp Asn Phe Leu Met Ala His Leu Ile Asn Glu Lys Asp Gly Glu
            100                 105                 110

Thr Phe Gln Leu Met Gly Leu Tyr Gly Arg Glu Pro Asp Leu Ser Ser
            115                 120                 125

Asp Ile Lys Glu Arg Phe Ala Gln Leu Cys Glu Glu His Gly Ile Leu
        130                 135                 140

Arg Glu Asn Ile Ile Asp Leu Ser Asn Ala Asn Arg Cys
145                 150                 155

<210> SEQ ID NO 6
<211> LENGTH: 159
<212> TYPE: PRT
<213> ORGANISM: Artificial Sequence
<220> FEATURE:
<223> OTHER INFORMATION: Description of Artificial Sequence:
      beta-protein (1epb)

<400> SEQUENCE: 6

Val Lys Asp Phe Asp Ile Ser Lys Phe Leu Gly Phe Trp Tyr Glu Ile
1               5                   10                  15

```
Ala Phe Ala Ser Lys Met Gly Thr Pro Gly Leu Ala His Lys Glu Glu
             20                  25                  30

Lys Met Gly Ala Met Val Val Glu Leu Lys Glu Asn Leu Leu Ala Leu
         35                  40                  45

Thr Thr Thr Tyr Tyr Ser Glu Asp His Cys Val Leu Glu Lys Val Thr
     50                  55                  60

Ala Thr Glu Gly Asp Gly Pro Ala Lys Phe Gln Val Thr Arg Leu Ser
 65                  70                  75                  80

Gly Lys Lys Glu Val Val Glu Ala Thr Asp Tyr Leu Thr Tyr Ala
             85                  90                  95

Ile Ile Asp Ile Thr Ser Leu Val Ala Gly Ala Val His Arg Thr Met
            100                 105                 110

Lys Leu Tyr Ser Arg Ser Leu Asp Asp Asn Gly Glu Ala Leu Tyr Asn
            115                 120                 125

Phe Arg Lys Ile Thr Ser Asp His Gly Phe Ser Glu Thr Asp Leu Tyr
            130                 135                 140

Ile Leu Lys His Asp Leu Thr Cys Val Lys Leu Gln Ser Ala Ala
145                 150                 155

<210> SEQ ID NO 7
<211> LENGTH: 153
<212> TYPE: PRT
<213> ORGANISM: Artificial Sequence
<220> FEATURE:
<223> OTHER INFORMATION: Description of Artificial Sequence:
      alpha-protein (1mbc)

<400> SEQUENCE: 7

Val Leu Ser Glu Gly Glu Trp Gln Leu Val Leu His Val Trp Ala Lys
 1               5                  10                  15

Val Glu Ala Asp Val Ala Gly His Gly Gln Asp Ile Leu Ile Arg Leu
             20                  25                  30

Phe Lys Ser His Pro Glu Thr Leu Glu Lys Phe Asp Arg Phe Lys His
         35                  40                  45

Leu Lys Thr Glu Ala Glu Met Lys Ala Ser Glu Asp Leu Lys Lys His
     50                  55                  60

Gly Val Thr Val Leu Thr Ala Leu Gly Ala Ile Leu Lys Lys Lys Gly
 65                  70                  75                  80

His His Glu Ala Glu Leu Lys Pro Leu Ala Gln Ser His Ala Thr Lys
             85                  90                  95

His Lys Ile Pro Ile Lys Tyr Leu Glu Phe Ile Ser Glu Ala Ile Ile
            100                 105                 110

His Val Leu His Ser Arg His Pro Gly Asp Phe Gly Ala Asp Ala Gln
            115                 120                 125

Gly Ala Met Asn Lys Ala Leu Glu Leu Phe Arg Lys Asp Ile Ala Ala
            130                 135                 140

Lys Tyr Lys Glu Leu Gly Tyr Gln Gly
145                 150

<210> SEQ ID NO 8
<211> LENGTH: 153
<212> TYPE: PRT
<213> ORGANISM: Artificial Sequence
<220> FEATURE:
<223> OTHER INFORMATION: Description of Artificial Sequence:
      alpha-protein 1gdi)

<400> SEQUENCE: 8
```

```
Gly Ala Leu Thr Glu Ser Gln Ala Ala Leu Val Lys Ser Ser Trp Glu
  1               5                  10                  15

Glu Phe Asn Ala Asn Ile Pro Lys His Thr His Arg Phe Phe Ile Leu
             20                  25                  30

Val Leu Glu Ile Ala Pro Ala Ala Lys Asp Leu Phe Ser Phe Leu Lys
         35                  40                  45

Gly Thr Ser Glu Val Pro Gln Asn Asn Pro Glu Leu Gln Ala His Ala
     50                  55                  60

Gly Lys Val Phe Lys Leu Val Tyr Glu Ala Ala Ile Gln Leu Glu Val
 65                  70                  75                  80

Thr Gly Val Val Val Thr Asp Ala Thr Leu Lys Asn Leu Gly Ser Val
             85                  90                  95

His Val Ser Lys Gly Val Ala Asp Ala His Phe Pro Val Val Lys Glu
            100                 105                 110

Ala Ile Leu Lys Thr Ile Lys Glu Val Val Gly Ala Lys Trp Ser Glu
            115                 120                 125

Glu Leu Asn Ser Ala Trp Thr Ile Ala Tyr Asp Glu Leu Ala Ile Val
        130                 135                 140

Ile Lys Lys Glu Met Asp Asp Ala Ala
145                 150

<210> SEQ ID NO 9
<211> LENGTH: 162
<212> TYPE: PRT
<213> ORGANISM: Artificial Sequence
<220> FEATURE:
<223> OTHER INFORMATION: Description of Artificial Sequence:
      alpha-protein (1cpc)

<400> SEQUENCE: 9

Met Lys Thr Pro Leu Thr Glu Ala Val Ala Ala Ala Asp Ser Gln Gly
  1               5                  10                  15

Arg Phe Leu Ser Ser Thr Glu Ile Gln Thr Ala Phe Gly Arg Phe Arg
             20                  25                  30

Gln Ala Ser Ala Ser Leu Ala Ala Ala Lys Ala Leu Thr Glu Lys Ala
         35                  40                  45

Ser Ser Leu Ala Ser Gly Ala Ala Asn Ala Val Tyr Ser Lys Phe Pro
     50                  55                  60

Tyr Thr Thr Ser Gln Asn Gly Pro Asn Phe Ala Ser Thr Gln Thr Gly
 65                  70                  75                  80

Lys Asp Lys Cys Val Arg Asp Ile Gly Tyr Tyr Leu Arg Met Val Thr
             85                  90                  95

Tyr Cys Leu Val Val Gly Gly Thr Gly Pro Leu Asp Asp Tyr Leu Ile
            100                 105                 110

Gly Gly Ile Ala Glu Ile Asn Arg Thr Glu Asp Leu Ser Pro Ser Trp
            115                 120                 125

Tyr Val Glu Ala Leu Lys Tyr Ile Lys Ala Asn His Gly Leu Ser Gly
        130                 135                 140

Asp Pro Ala Val Glu Ala Asn Ser Tyr Ile Asp Tyr Ala Ile Asn Ala
145                 150                 155                 160

Leu Ser

<210> SEQ ID NO 10
<211> LENGTH: 152
<212> TYPE: PRT
<213> ORGANISM: Artificial Sequence
```

-continued

```
<220> FEATURE:
<223> OTHER INFORMATION: Description of Artificial Sequence:
      alpha-protein (1mbc)

<400> SEQUENCE: 10

Val Leu Ser Glu Gly Glu Trp Gln Leu Val Leu His Val Trp Ala Lys
 1               5                  10                  15

Val Glu Ala Asp Val Ala Gly His Gly Gln Asp Ile Leu Ile Arg Leu
            20                  25                  30

Phe Lys Ser His Pro Glu Thr Leu Glu Lys Phe Asp Arg Phe Lys His
            35                  40                  45

Leu Lys Thr Glu Ala Glu Met Lys Ala Ser Glu Asp Leu Lys Lys His
        50                  55                  60

Gly Val Thr Val Leu Thr Ala Leu Gly Ala Ile Leu Lys Lys Lys Gly
 65                  70                  75                  80

His His Glu Ala Glu Leu Lys Pro Leu Ala Gln Ser His Ala Thr Lys
                85                  90                  95

His Lys Ile Pro Ile Lys Tyr Leu Glu Phe Ile Ser Glu Ala Ile Ile
                100                 105                 110

His Val Leu His Ser His Pro Gly Asp Phe Gly Ala Asp Ala Gln Gly
            115                 120                 125

Ala Met Asn Lys Ala Leu Glu Leu Phe Arg Lys Asp Ile Ala Ala Lys
        130                 135                 140

Tyr Lys Glu Leu Gly Tyr Gln Gly
145                 150
```

STRUCTURAL ALIGNMENT METHOD MAKING USE OF A DOUBLE DYNAMIC PROGRAMMING ALGORITHM

BACKGROUND OF THE INVENTION

1. Fields of the Invention

The present invention relates to the method for a structural alignment with a double dynamic programming algorithm. The method is suitable for comparative analysis of protein structures in order to obtain information about the structure, function and evolution of the proteins.

2. Description of the Related Art

Proteins are major components of living organisms, which are involved in various aspects of biological activities. Ordinarily, living organisms use 20 kinds of amino acids as the components of proteins. The amino acids are sequentially connected by peptide bonds to form proteins. The amino acid sequence of a protein folds into a tertiary structure to exert its activity.

The databases for the amino acid sequences and tertiary structures have grown quite rapidly, due to the recent development in the techniques for determining nucleotide sequences of DNAs and those for the tertiary structures of proteins. In order to manage and analyze a huge amount of sequence and structure data, computers have been introduced into the field of molecular biology. Then, an interdisciplinary area between information science and molecular biology, so called, "computational molecular biology" or "bioinformatics", has been developed. In the area, comparative analysis of proteins occupies an important position as a method to extract structural and functional information of proteins. It is known that two proteins are similar in sequence and/or structure to each other, when they share a common ancestral genes or a common functional constraints. Conversely, we can obtain functional, structural, and/or evolutionary information through comparison of similar sequences or similar structures.

Alignment is a basic operation for comparative study, which produces residue-to-residue correspondence among similar biological macromolecules. In the procedure, a residue of a protein is disposed in parallel to show the correspondence. The residues without equivalent ones are aligned with empty marks called "gap". Alignment is classified into three types, (1) sequence alignment, (2) threading (comparison between sequence and structure), and (3) structural alignment. Sequence alignment is a major tool for sequence analysis and is widely utilized in the field of molecular biology. The invention of threading is relatively recent, which is used to search for sequences to suit a given tertiary structure. However, the method still has many problems in the accuracy of the alignment and the reliability of the prediction. In both approaches, residue-to-residue correspondence is produced by a method called "dynamic programming algorithm (DP)". The detail of the method will be described below. The invention of the structural alignment is also relatively recent, and the DP also occupies an important position to generate residue-to-residue correspondence in the structural alignment. Considering the rapid growth of structure database, it is expected that the structural alignment will be an important tool for the structure analysis.

FIG. 1 shows the idea of structural alignment. Consider two proteins shown in FIG. 1, proteins A and B. Protein A has an amino acid sequence, N-terminus-A-C-E-L-S-I-S-R-N-Y-D-T-I-P-D-C-terminus (SEQ ID no:1). The capital letters indicate one letter expression of amino acid residues. The amino acid sequence folds into a structure shown in FIG. 1(a). Similarly, protein B, whose amino acid sequence is N-terminus-V-A-S-Q-I-G-W-D-E-D-I-H-L-E-P-I-G-E-S-C-terminus (SEQ ID no:2), folds into a structure shown in FIG. 1(b). The figures suggest that the fold of protein A is similar to that of protein B. Structural alignment automatically detects the structurally equivalent residues between the proteins, and produce the residue-to-residue correspondence as follows;

A-CELSISR--NYD-TIPD SEQ ID no:1

VASQIGWDEDIHLEPIGES SEQ ID no:2 where '-' indicates a gap.

Many methods have been elaborated for the structural alignment. Some of them do not use DP. However, any methods suffer a common problem, that is, it requires a huge amount of computational time to construct a structural alignment. The present inventors have developed a technique to reduce the computational time by introducing two approximations into the double dynamic programming algorithm (DDP).

DDP is an algorithm for the structural alignment, which was invented by Taylor and Orengo in 1989. The algorithm is regarded as an extension of DP used for sequence alignment and threading. To facilitate the understanding of DDP, the explanation of DDP will be started from the description of DP. Consider two similar amino acid sequences. In order to align the sequences, a two-dimensional matrix, D, is required. FIG. 2 shows the matrix D. The upper left corner of the matrix corresponds with the N-termini of the proteins. Each residue of protein A corresponds with a row of the matrix, according to the order in the primary structure. Similarly, each residue of protein B corresponds with a column of the matrix. The elements of the matrix are successively determined by solving the recurrence equation as follows;

$$D(i,j)=\max\{s(i,j)+D(i-1,j-1), D(i-1,j)-\beta, D(i,j-1)-\beta\}$$

where $\beta$ is a gap penalty, and $s(i, j)$ is the similarity between the amino acid residue i of protein A and the residue j of protein B. The set of the numerical value indicating the similarity between every pair of amino acid residues is called "score table". The greater the similarity between an amino acid pair is, the larger the value is. The value of $s(i, j)$ is obtained from a score table. Then, the three arguments in the recurrence equation correspond to three different operations; i.e., (1) connecting residue pairs in a diagonal direction without inserting gap, (2) inserting a gap in a corresponding row, and (3) inserting a gap in a corresponding column. These operations, (1)–(3), also indicate the movements in diagonal, horizontal and vertical directions on the matrix. By solving the equation, the numerical values are accumulated from the upper left toward the lower right in the matrix D. At the same time, the selection of the arguments in the Max operation, that is, the movement on the matrix, are stored in another two-dimensional matrix with the same size as the matrix D. The matrix is called "path matrix", which makes it easy to do back tracking. The numerical value of the lower right corner of the matrix D suggests that the similarity between two amino acid sequences. From the corner, back tracking is performed using the path matrix. Then, an optimal alignment or residue-to-residue correspondence is generated. The time complexity for the calculation is $O(L^2M+LM^2)$, where L and M are the lengths of proteins A and B.

DDP is basically the same as DP (see FIG. 3), although the subjects of DDP are the tertiary structures of proteins.

Like the case of DP, DDP requires a two-dimensional matrix, D, and each residue of the structures under consideration are also corresponded with a row or a column of the matrix. Then, a recurrence equation, which is similar to that for DP described above, is solved. However, s(i, j) is not the similarity between two amino acid residues, but represents the similarity in structural environments between residues i and j.

FIG. 4 shows the definition of structural environment of a residue, which was given by Taylor and Orengo in 1989. They defined the structural environment of amino acid residue i of protein A as a set of vectors from β-carbon of the residue i to those of all the other residues in the proteins. That is, the structural environment of a residue i indicates the relative position of the residue i in the protein A. The similarity in structural environment between two residues is evaluated by DP. As shown in FIG. 5, a two-dimensional matrix is required for the evaluation. Like the case of sequence alignment, each vector constituting the structural environments is corresponded with a row or a column of the two-dimensional matrix, according to the order in the primary structure. Then, similar recurrence equation is solved, and the scores are also accumulated from upper left toward the lower right. However, the similarity between two vectors, say x and y, is calculated by the equation shown in the FIG. 5. Through analogy, the value stored in the lower right corner of the matrix D is considered to indicate the similarity in structural environment between two residues. Therefore, the value is used as s(i, j) shown in FIG. 3.

FIG. 6 summarizes the procedure of structural alignment by DDP. As shown in the figure, DP is used for two different stages of the calculation. The DP to evaluate the similarity in structural environment is called "lower level DP", while the DP to make residue-to-residue correspondence is called "upper level DP". It is the reason why the method is called Double Dynamic Programming algorithm, DDP. The time complexity of the calculation is estimated to be $O(L^3M^2+L^2M^3)$, which is greater than that of sequence alignment, $O(L^2M+LM^2)$. That is, the computational time is one of the major constraints of the structural alignment by DDP. Therefore, Taylor and Orengo, the inventors of DDP, have improved the method, focusing on this point (see FIG. 7).

At first, they introduced a window into the matrix D, and applied DDP calculation to the residue pairs within the window (FIG. 7(a)). Next, they further restricted residue pairs by selecting those having similar torsional angles and surface areas within the window (FIG. 7(b)). In their latest approach, they aligned secondary structures at first. Then, they selected residues pairs within the aligned secondary structures and with similar torsional angles and surface areas. Thus, they have reduced the computational time by restricting residue pairs to which DDP calculation is applied. Their improvements have remarkably reduced the computational time. However, the methods include many complicated and time-consuming procedures before actual structural alignment such as the assignment and alignment of secondary structures, and the assignment and comparison of torsional angles and surface areas.

SUMMARY OF THE INVENTION

In view of the foregoing problems, an object of the present invention is to provide a structural alignment method making use of double dynamic programming algorithm, which is simpler than conventional methods, and which can shorten computational time while maintaining high accuracy.

In order to achieve the object, the present invention provides an improved structural alignment method making use of double dynamic programming algorithm, which method comprises the steps of:

performing distance cut-off approximation in which a sphere having a predetermined radius r and centered at the side chain of a residue i of a protein is defined, and residues with side chain centers that are present within the sphere are selected as constituent elements of a structural environment of the residue i; and performing ΔN cut-off approximation to select residue pairs with similar number of residues constituting the local environments.

Preferably, the radius r is 10 to 15 angstroms, and ΔN is 10.

Preferably, double dynamic programming algorithm is performed only for residue pairs within an ε-suboptimal region determined by the above structural alignment method, without introduction of approximation.

In the method of structural alignment according to the present invention, structural alignment can be performed in a simplified manner in a shortened period of time, while high accuracy is maintained.

Proteins with a similar folding pattern often share a similar function. Therefore, the detection and comparison of similar folds would bring great insight into the functions of proteins. The method of structural alignment of the present invention, together with its possible extensions, is helpful for such comparative studies. Database searching is a straightforward extension of a programmed implementation, which could detect similar folds to query coordinates. If similar folds are detected, a multiple structural alignment may be performed by a program as an extension of the present invention. As a result, it is possible to detect residue-to-residue correspondence, from which the details of functionally conserved sites and diverged sites reflecting the functional difference may be studied. An exemplary benefit of the structural comparison is that residue-to-residue correspondence may be detected if the tertiary structures are similar. Similarity in amino acid sequence is not required for the method of the present invention.

Comparative studies are important in drug design. In the field of pharmacology, structure-based drug design is considered a novel approach. The method of the present invention could be utilized, for example, by first considering a protein whose structure has been determined. If no drug affecting the structure has yet been identified, then the structure which has been identified could be compared with coordinates available in a protein structure database, using the method of the present invention. If proteins with similar folds are detected, and if drugs against the similar proteins have already been identified, then drugs against the considered protein may be designed based on the knowledge of the drugs against the proteins having similar folds. The method of the present invention may also be useful, for example, for the design of artificial proteins.

BRIEF DESCRIPTION OF THE DRAWINGS

FIG. 4 is an explanatory diagram showing the definition of the structural environment of residue i of a protein;

FIG. 5 is a diagram showing the similarity in structural environment between residues i and j;

FIG. 9 is a diagram showing the concept of ΔN cut-off approximation according to the present invention;

FIG. 22 is a table showing four cases where the cut-off distance is set to 12 angstroms and ΔN is set to 10;

FIG. 23 is an alignment for Case 1 (β-protein 7fab1 (SEQ ID no:3), 7fabh (SEQ ID no:4));

FIG. 24 is an alignment for Case 2 (β-protein 1mup (SEQ ID no:5), 1eph (SEQ ID no:6));

FIG. 25 is an alignment for Case 3 (α-protein 1mbc (SEQ ID no:7), 1gdi (SEQ ID no:8));

FIG. 26 is an alignment for Case 4 (α-protein 1mbc (SEQ ID no:10), 1cpc (SEQ ID no:9));

FIG. 27 is a table showing the results of alignment performed for the four cases shown in FIG. 22 in order to explain the difference between rough alignment and alignment with full structural environment;

FIG. 28 is a table showing the results of alignment performed for the four cases shown in FIG. 22 in order to explain the difference between two-step alignment and full structural environment alignment; and FIGS. 29–31 are flowcharts showing the processing for structural alignment according to the present invention.

DESCRIPTION OF THE PREFERRED EMBODIMENT

An embodiment of the present invention will next be described in detail with reference to the drawings.

First, structural alignment by double dynamic programming algorithm (DDP) of the present invention will be described in detail.

In the method of the present invention, two kinds of approximation are utilized. The present inventors have developed a program that is based on two approximations and that employs two-step alignment as needed in order to maintain accuracy of alignment.

(A) Distance Cut-off Approximation:

In order to express the structural environment of a residue of a protein, Taylor, Orengo, et al. have utilized all other residues of the protein. Therefore, the same amount of calculation (computation) as for sequence alignment is required for each lower-level DP, resulting in an increase in computational time.

In the present invention, the concept of distance cut-off approximation is introduced in order to shorten the computational time of the lower-level DP.

Figure 1B:
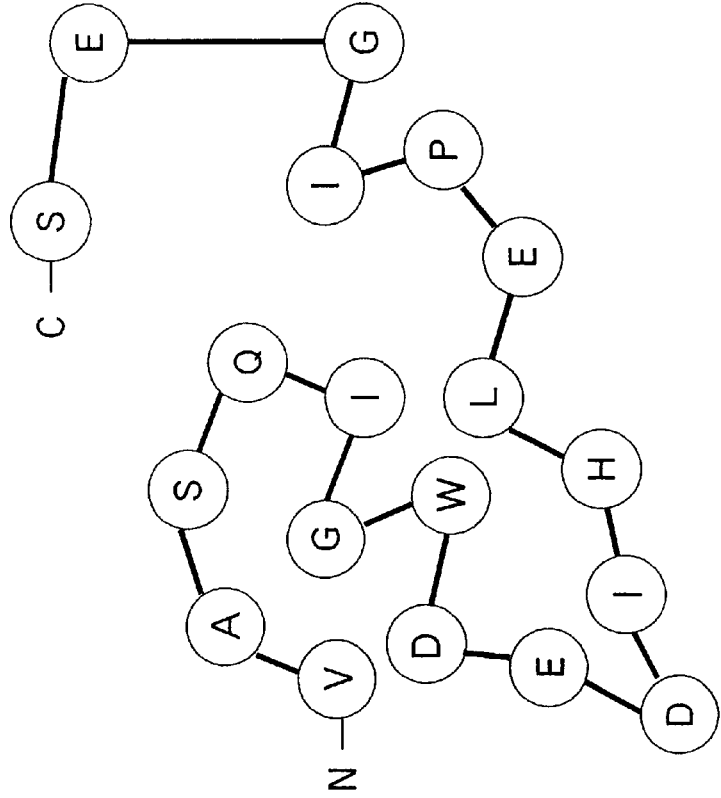
FIGS. 1(a) (SEQ ID no:1) and 1(b) (SEQ ID no:2) are diagrams showing an example of a conventional structural alignment method for proteins.
Figure 1A:
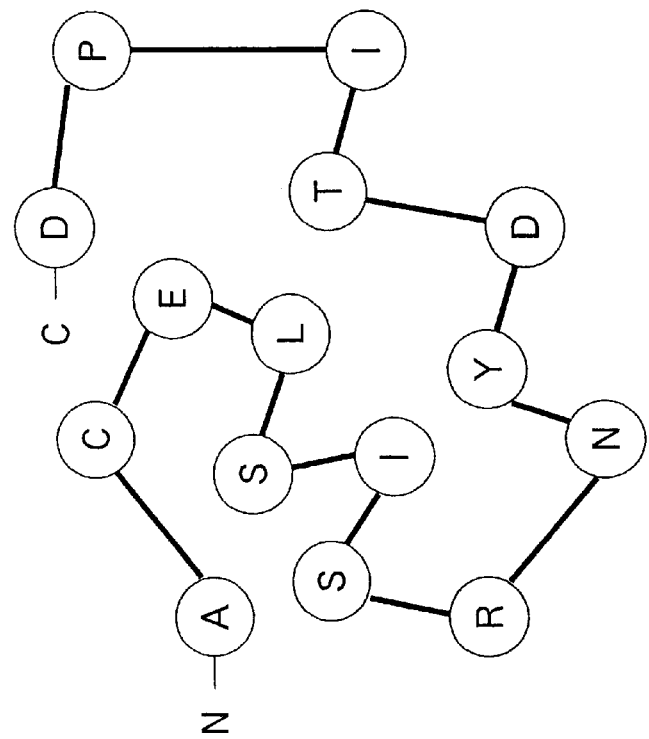
Figure 2:
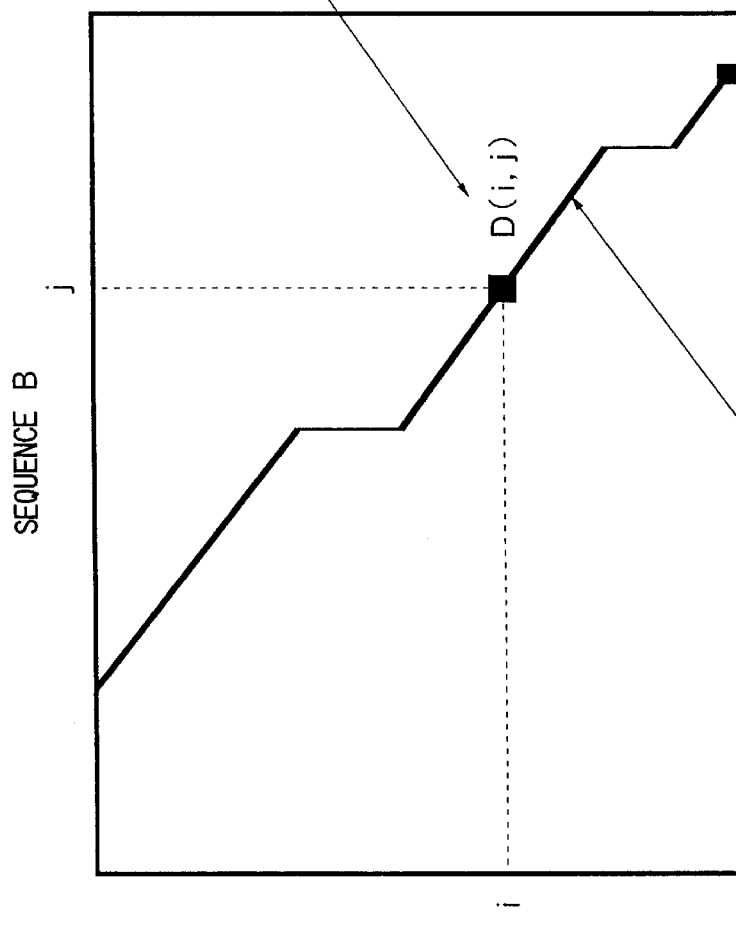
FIG. 2 is a diagram for explaining a recurrent equation for two-dimensional matrix DP.
Figure 3:
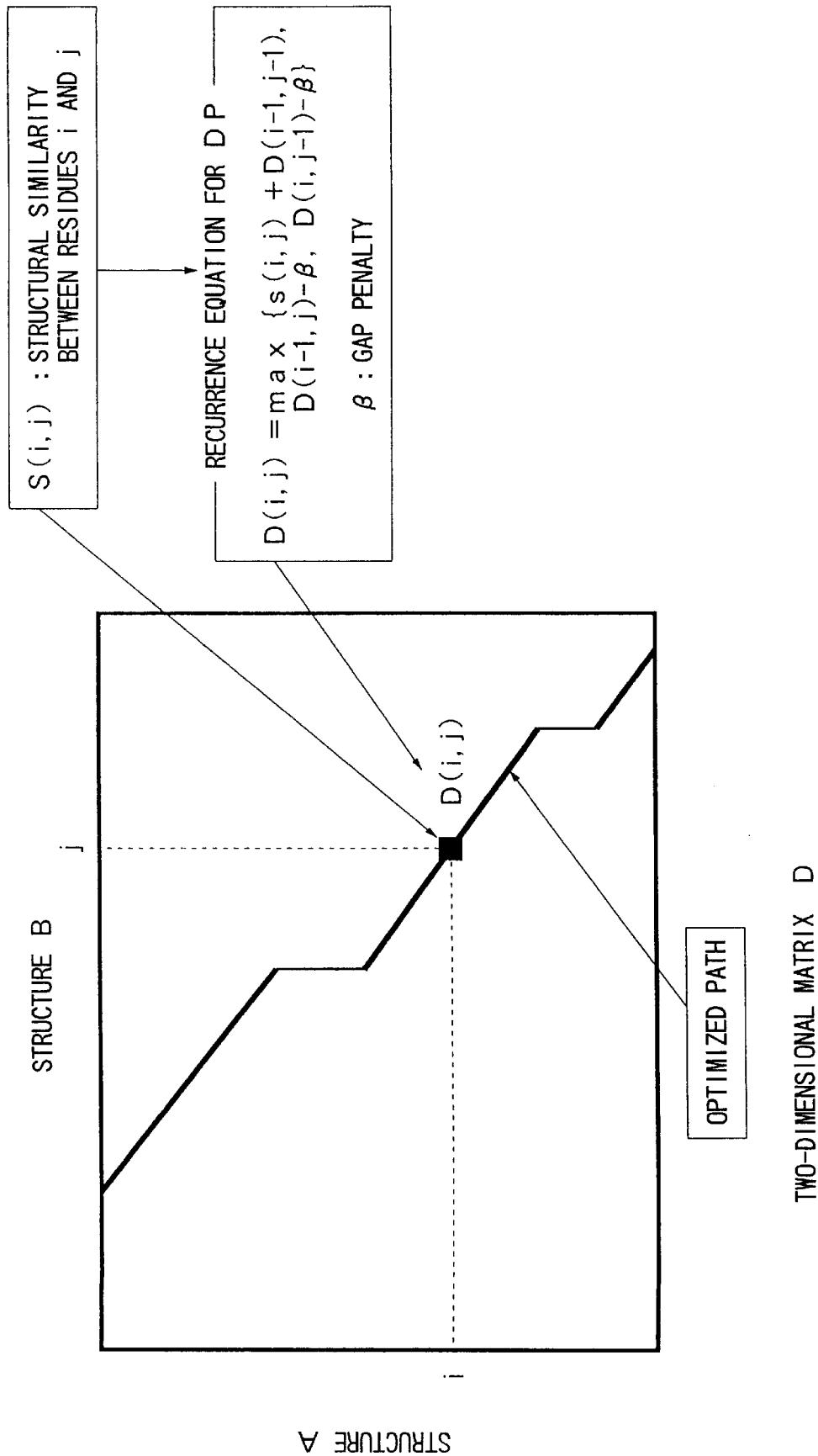
FIG. 3 is an explanatory diagram showing structural alignment proposed by Taylor and Orengo (1989)
Figure 6:
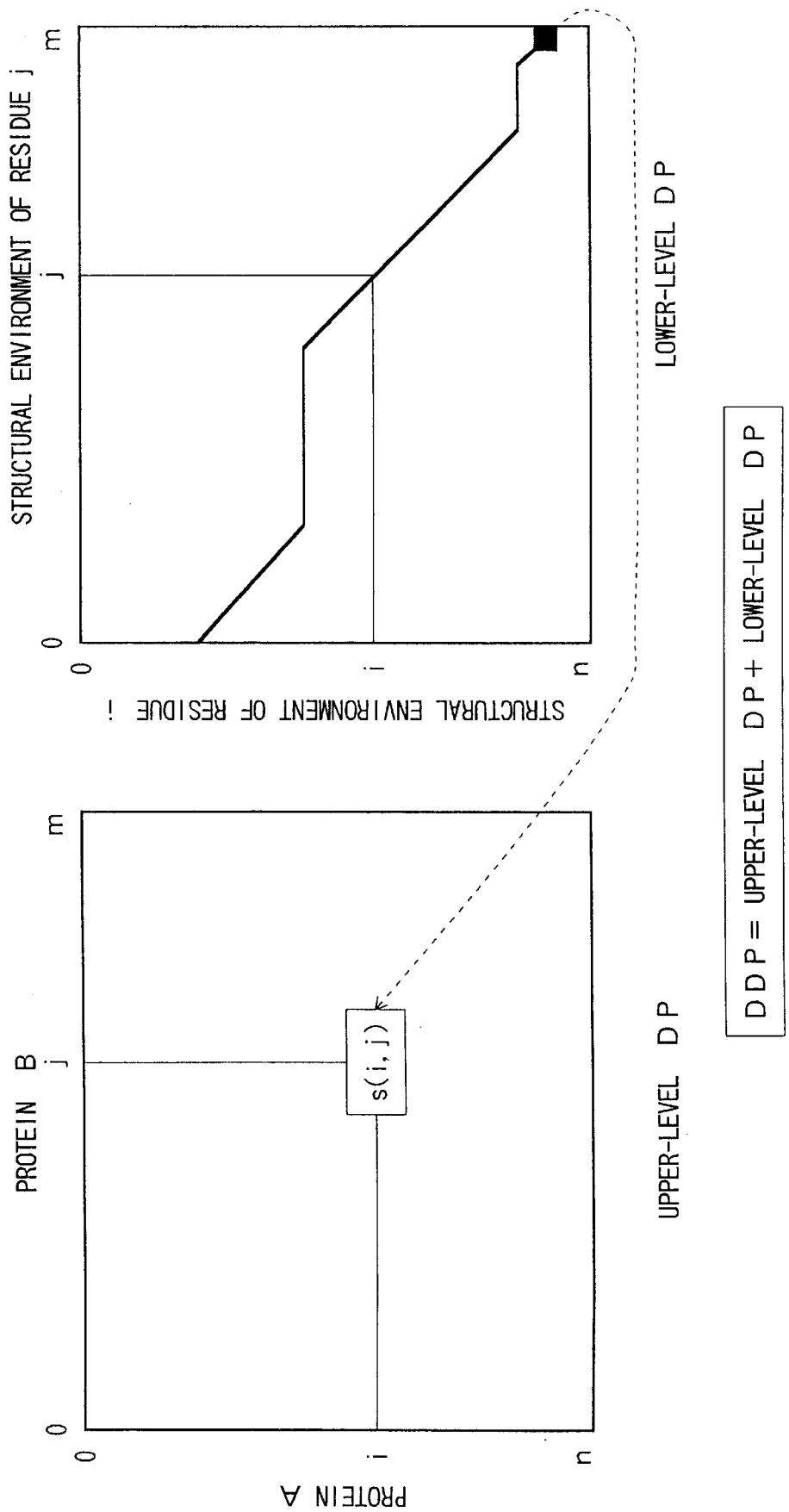
FIG. 6 is a diagram for explaining double dynamic programming algorithm.
Figure 7:
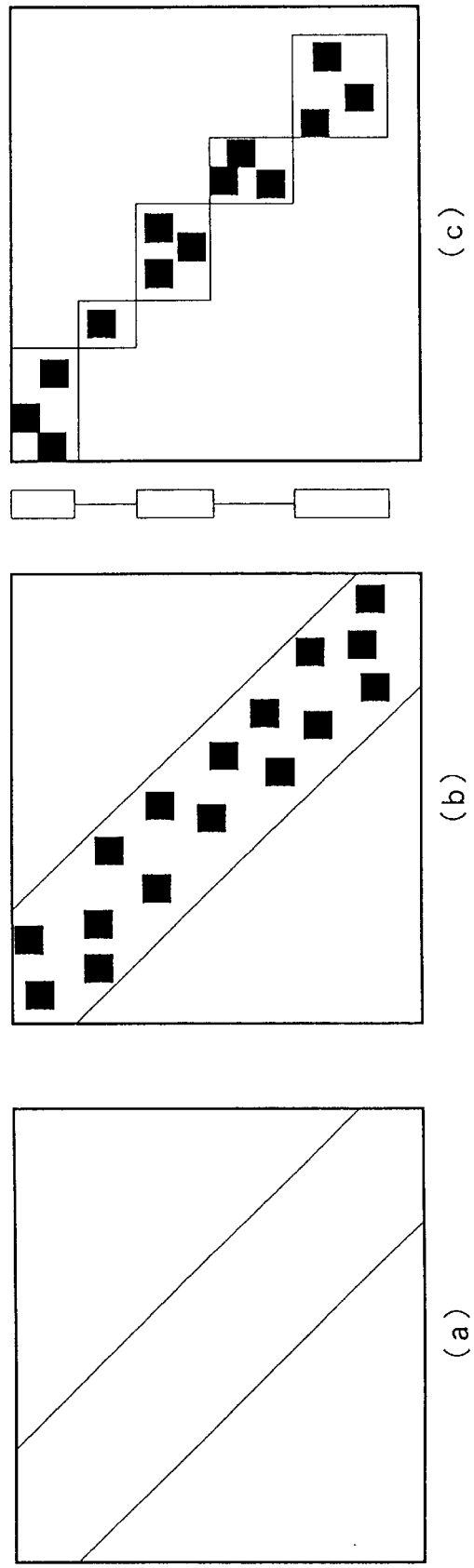
FIG. 7 is a diagram showing a method proposed by Taylor and Orengo for shortening computational time.
Figure 8:
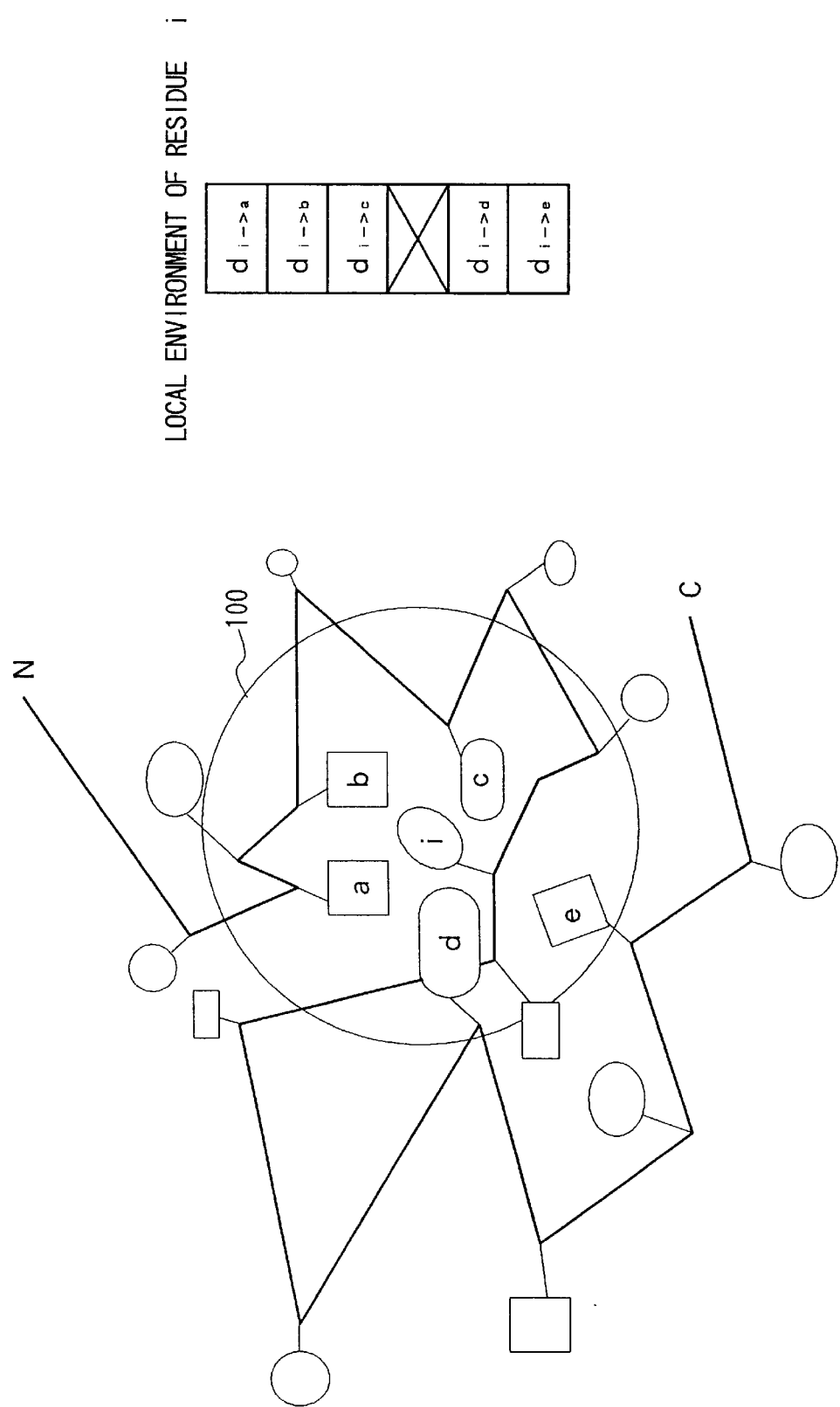
FIG. 8 is a diagram showing the concept of distance cut-off approximation according to the present invention.

FIG. 8 shows the concept of distance cut-off approximation.

In FIG. 8, numeral 100 denotes a sphere having a predetermined radius r and centered at the side chain of residue i of a protein. Residues with side chain centers that are present within the sphere are selected as constituent elements of a structural environment of the residue i. This structural environment for approximation is called a "local environment." The local environment is represented by a set of the distance between the center of the side chain of residue i and those of the remaining residues. As in the case of conventional DDP, the similarity between two local environments is calculated by DP. This DP serves as the lower-level DP in the method of the present invention. The radius r of the sphere 100 is called a cut-off distance.

(B) ΔN Cut-off Approximation:

If two local environments resemble each other, the number of residues that constitute one local environment can be expected to be similar to the number of residues that constitute the other local environment. The principle of ΔN cut-off approximation is based on this idea.

FIG. 9 illustrates the principle of ΔN cut-off approximation.

The residues that constitute the local environment of residue i of protein A are divided into two groups, one of which includes residues located on the N-terminal side with respect to residue i and the other of which includes residues located on the C-terminal side with respect to residue i. The number of the residues located on the N-terminal side is represented by Nn(i,A), while the number of residues located on the C-terminal side is represented by Nc(i,A). Similarly, Nn(j,B) and Nc(j,B) are defined for the local environment of residue j of protein B.

For comparison between the local environments of residues i and j, comparison between Nn(i,A) and Nn(j,B) and that between Nc(i,A) and Nc(j,B) are first performed. If difference between Nn(i,A) and Nn(j,B) or that between Nc(i,A) and Nc(j,B) is equal to or greater than a threshold ΔN, the two local environments are judged not to resemble each other. In this case, lower-level DP is skipped, and s(i,j) used in upper-level DP is set to 0.0. If the difference is not greater than ΔN, s(i,j) is calculated by the lower-level DP. This operation enables selective comparison only for residue pairs having similar local environments.

(C) Two-Step Alignment:

The introduction of the two kinds of approximation described above reduces computational time, thereby providing an effect of some degree. However, alignment accuracy decreases. In order to solve this drawback, alignment accuracy is maintained through reproduction of an alignment, which is performed by the method shown in FIG. 10 based on an alignment generated through approximations.

Figure 10:
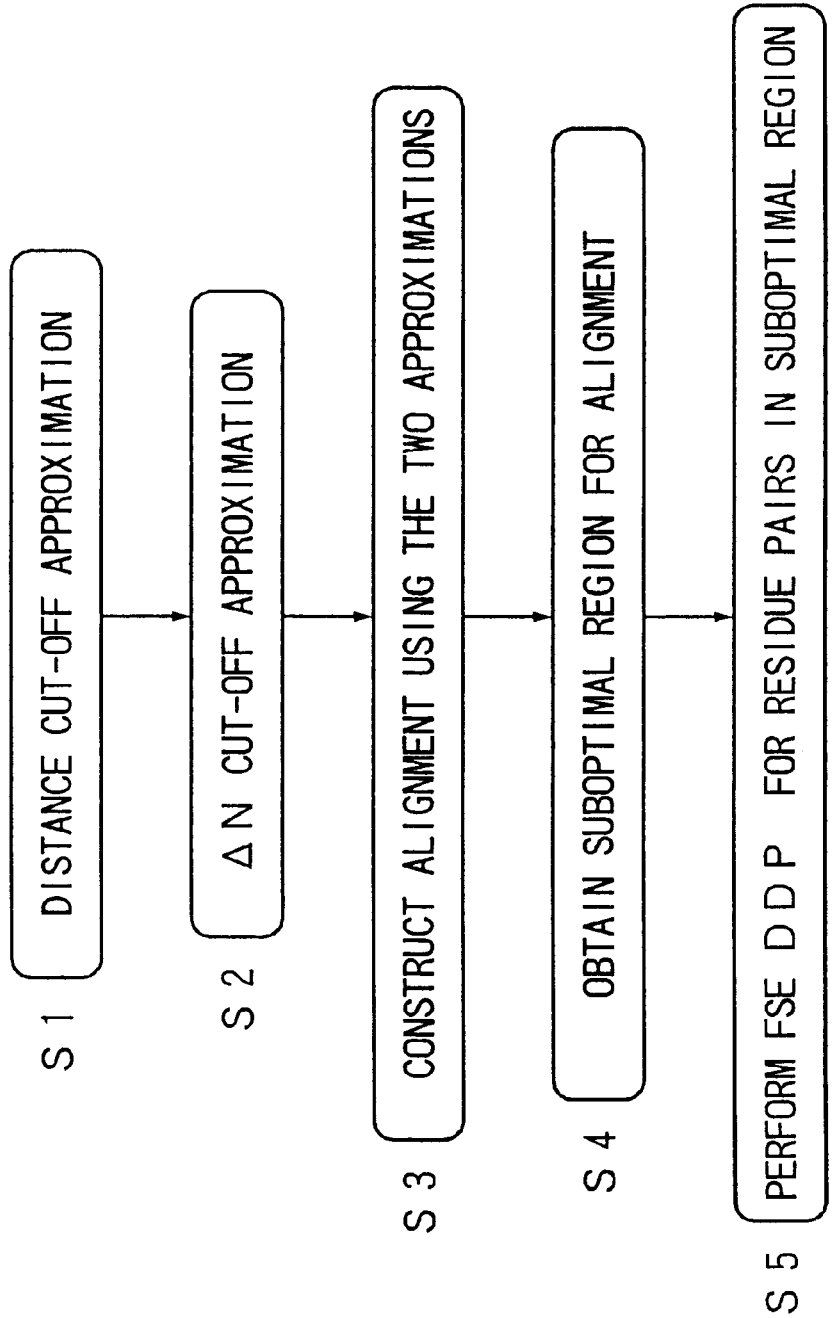
FIG. 10 is a flowchart of two-step alignment according to the present invention.

FIG. 10 is a general flow chart showing structural alignment making use of double dynamic programming according to the present invention.

In step S1, distance cut-off approximation is performed.

In step S2, ΔN cut-off approximation is performed.

In step S3, an alignment is produced based on the results of distance cut-off approximation and ΔN cut-off approximation.

In step 4, an ε-suboptimal region defined by the obtained approximate solutions is determined.

In step 5, DDP based on full structural environments (FSE) is performed for residue pairs within the ε-suboptimal region.

Figure 11:
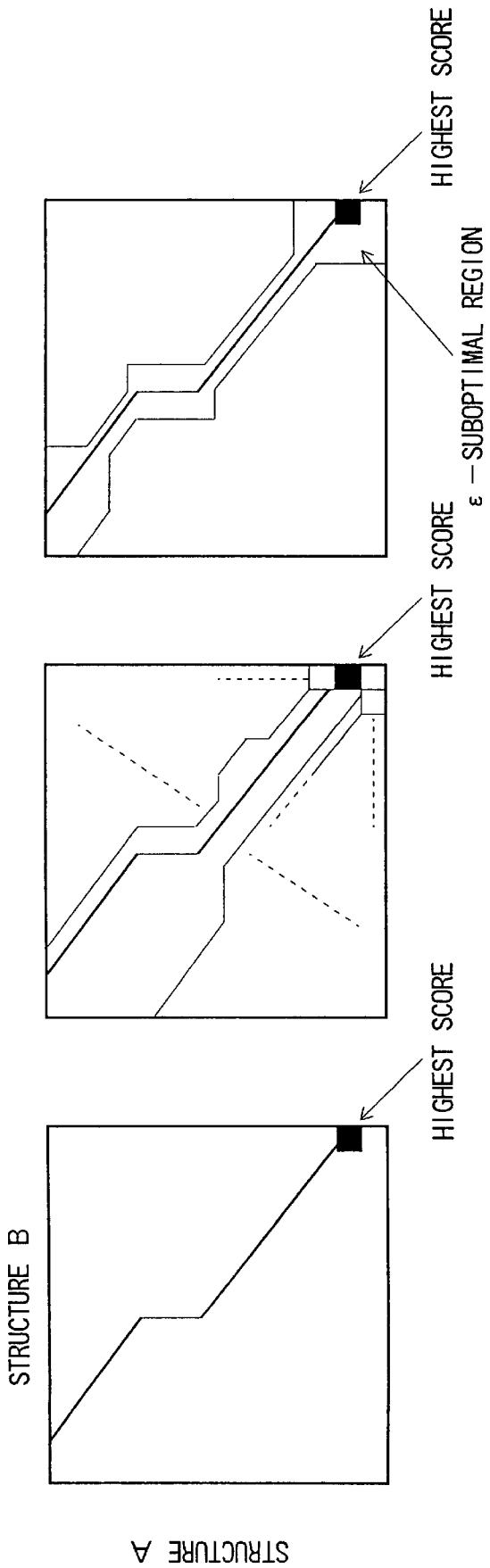
FIG. 11 is an explanatory diagram showing an ε-suboptimal region.
Figure 12:
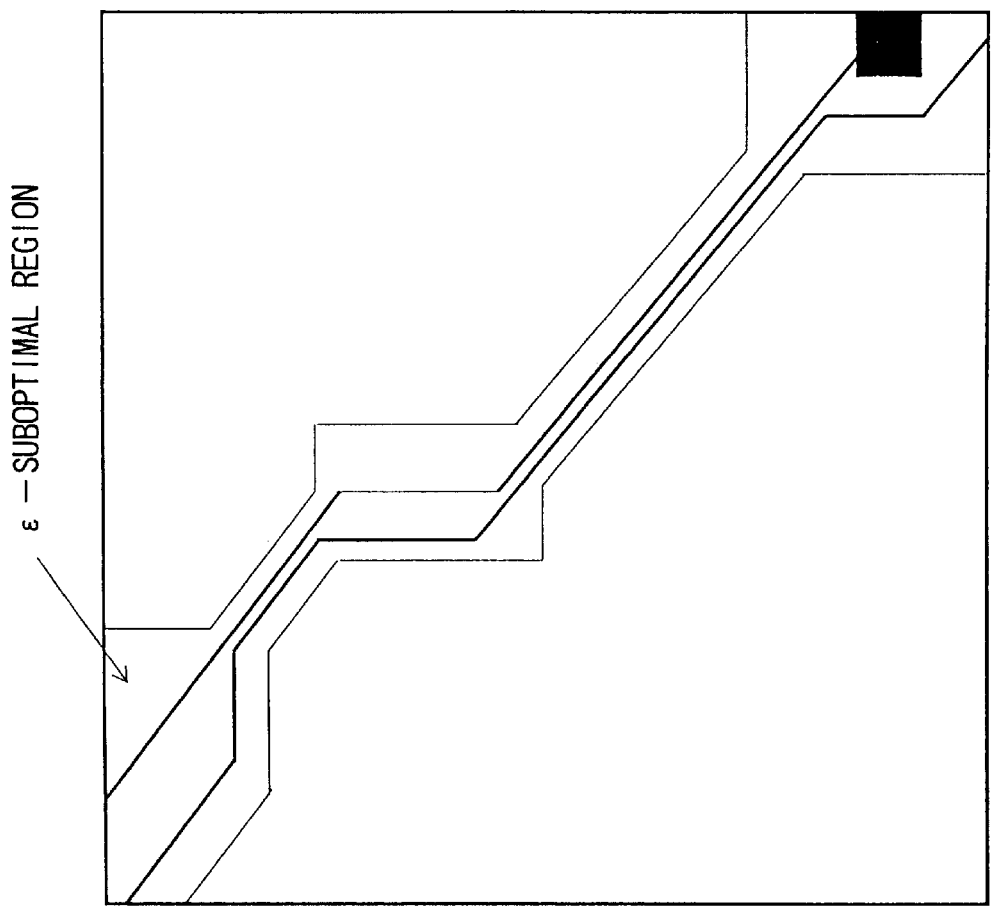
FIG. 12 is a diagram showing application of DDP calculation based on entire structural environment.
Figure 13:
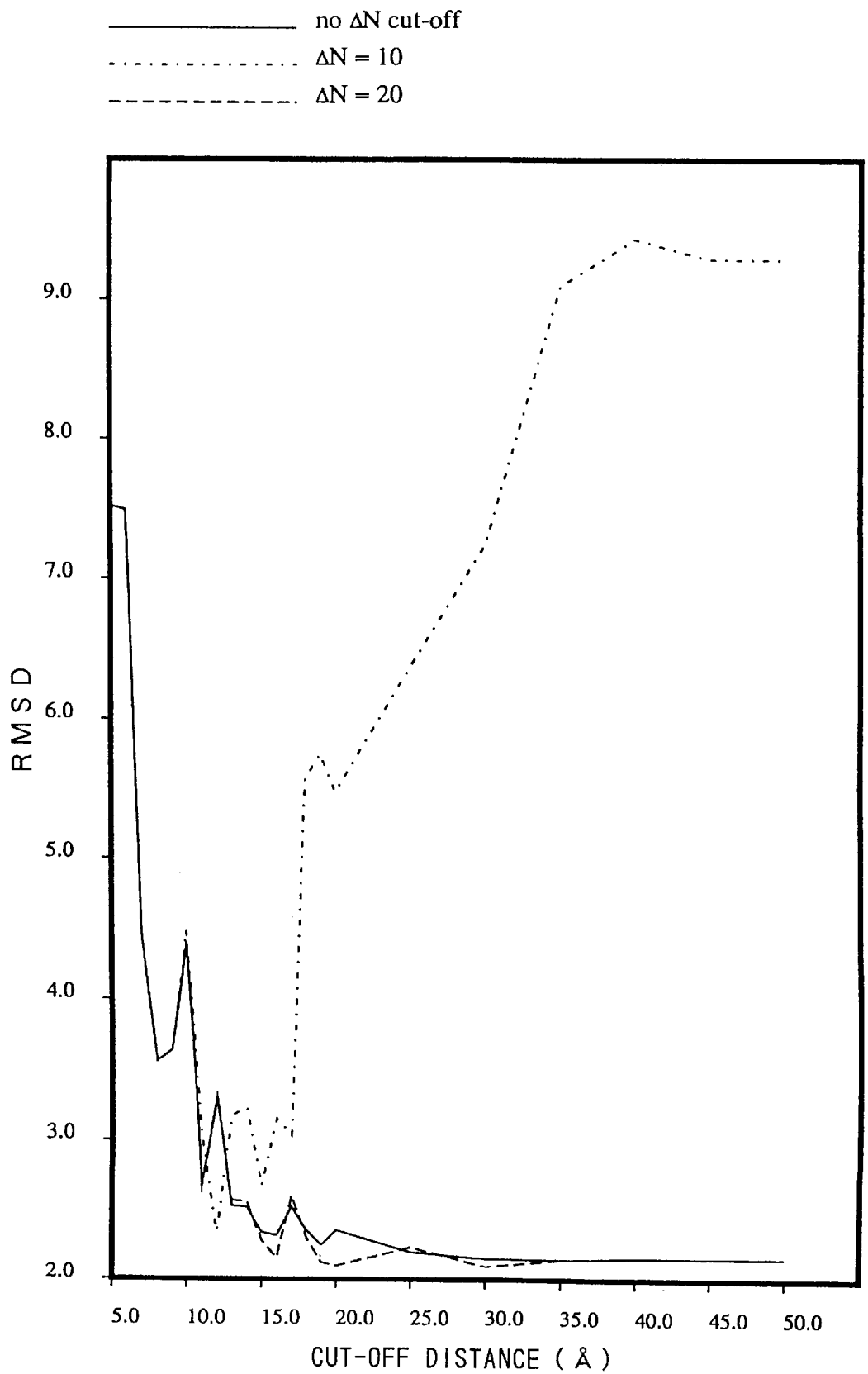
FIGS. 13–16 are plots each showing the relationship between degree of approximation and alignment accuracy.
Figure 14:
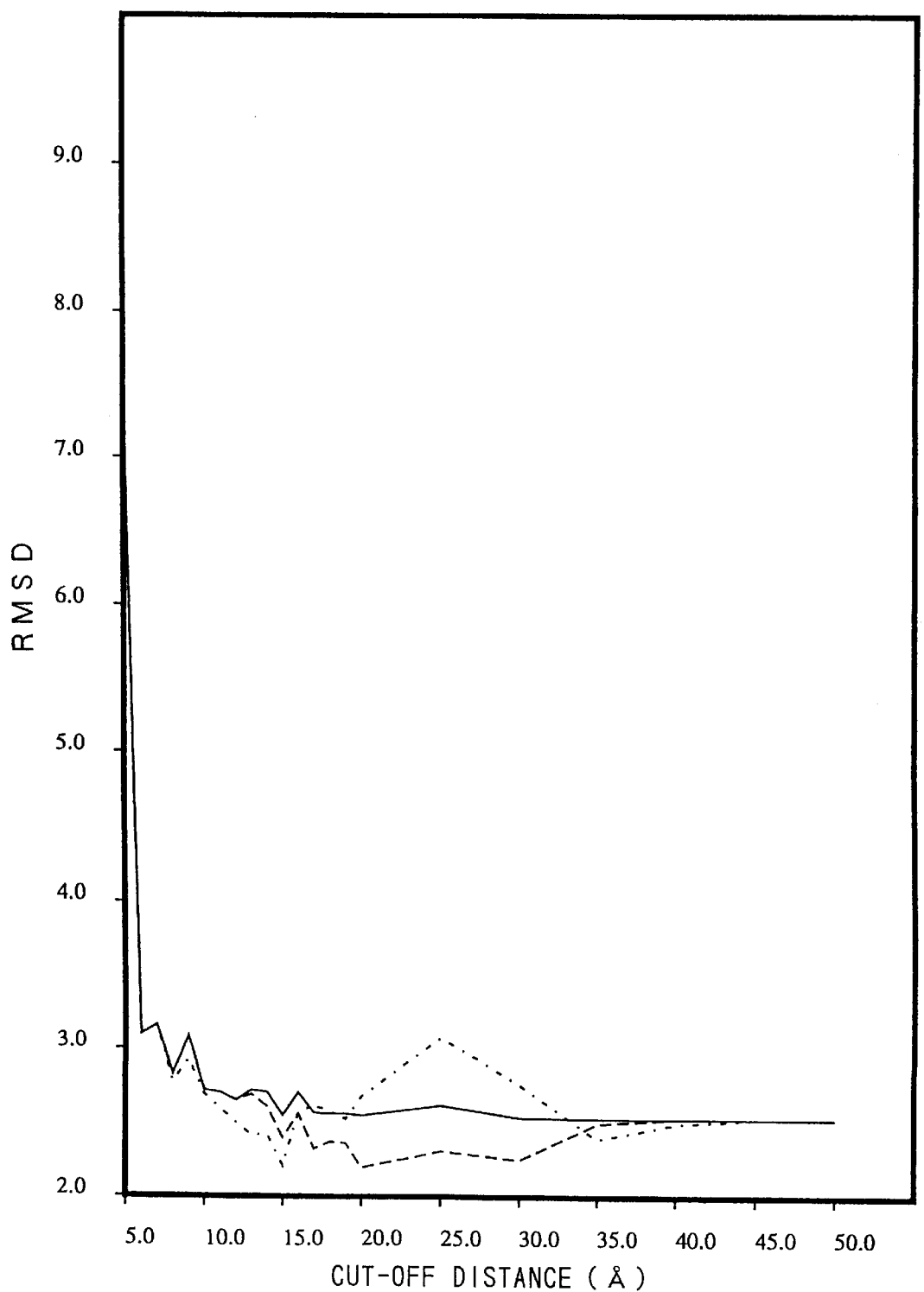
Figure 15:
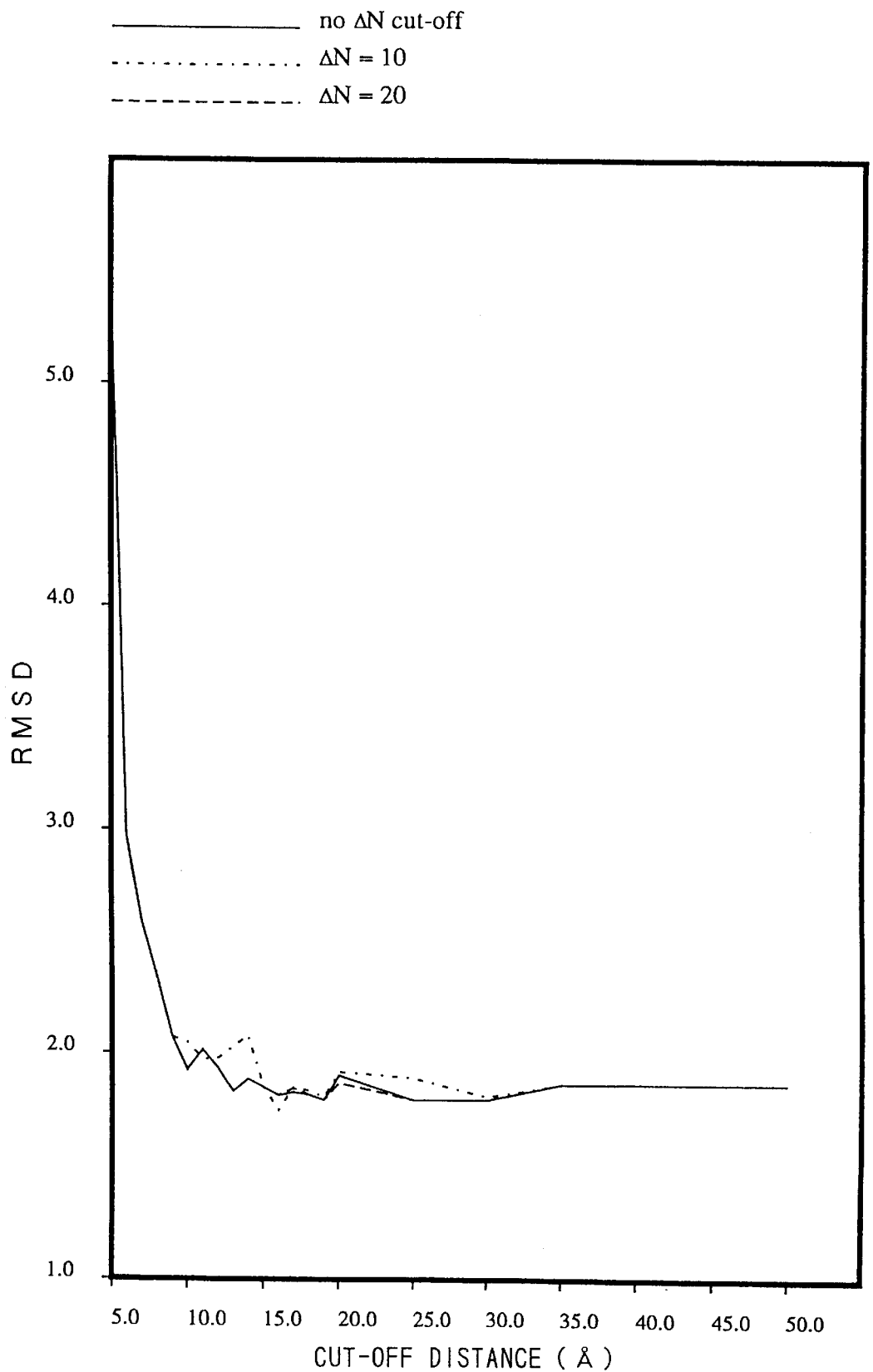
Figure 16:
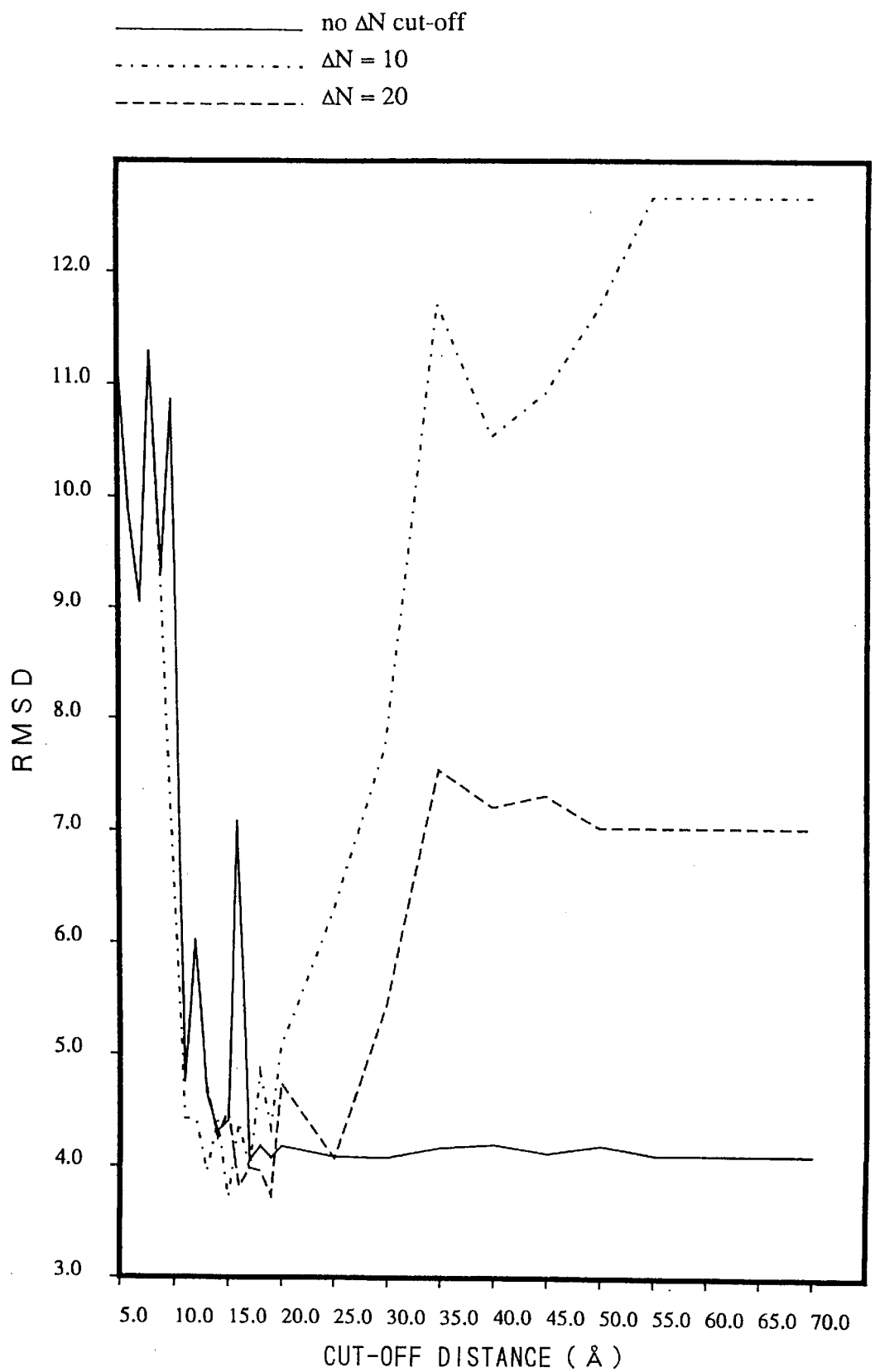

A description will now be given of the ε-suboptimal region with reference to FIGS. 11 and 12.

As described above, an optimal alignment is obtained by back tracking from an element with the highest score in the matrix D. However, it is possible to perform back tracking from any elements at lower right of the matrix D. Needless to say, the elements store the scores less than the highest score. Then, many other alternative alignments can be obtained by the back tracking. The ε-suboptimal region is defined as a set of such paths with scores deviated from less than ε from the highest score. It is known that the width of the suboptimal region corresponds with the reliability of the alignment. When the suboptimal region is wide, the reliability of the path in the region is considered to be low. On the other hand, the path in the suboptimal region is regarded as being reliable, when the region is narrow. As described above, the alignment made by DDP with the approximations resembles that without approximations. Therefore, an optimal path for an alignment calculated without approximations is expected to locate in the vicinity of the path for the alignment calculated with the approximations. In other words, the optimal path for the alignment made without approximations is expected to be included in the ε-suboptimal region of the alignment made with the approximations.

Therefore, we constructed a rough alignment at first, using two approximations, distance cutoff and ΔN cutoff. Then, the ε-suboptimal region for the rough alignment was calculated. Finally, the residue pairs within the suboptimal region is again applied to the DDP calculation. However, in the second step, the two approximations were not introduced into the DDP calculation, and the structural environments are fully described for the residues under consideration, that is, no distance cutoff or no ΔN cutoff. Hereafter, the structural environment without the approximation is called "full structural environment" (FSE). The algorithm proposed by Vingron & Argos was used to obtain the ε-suboptimal region.

Unlike the case of ordinary sequence analysis, the value of s(i,j) varies depending on cut-off distance, and therefore it is difficult to set the value of ε to a constant. Therefore, during the approximate alignment the standard deviation σ of the values of s(i,j) is obtained and employed as the unit for ε.

The results of application of the present invention and observations will be described below.

(A) Effect of Introduction of Approximations and Determination of a Proper Cut-off Distance and ΔN The effect of introduction of approximations was examined in terms of accuracy of alignment and computational time. For the examination, the method of the present invention was applied to four pairs of proteins shown in Table 1 (FIG. 22).

FIGS. 13–16 show the relationship between degree of approximation (cut-off distance) and alignment accuracy. Alignment accuracy was measured as a root mean square distance (RMSD). The vertical axis represents the RMSD and the horizontal axis represents the cut-off distance. The type of line is changed in accordance with the value of ΔN. This measurement was performed every 1 angstrom when the cut-off distance was in the range of 5 to 20 angstroms, and every 5 angstroms thereafter. The cut-off distance corresponding to the rightmost ends of the lines was set such that all molecules were included in the distance cut-off sphere (i.e., no distance cut-off).

As shown in these drawings, the shapes of the plots with different ΔN values in the cut-off distance from 5 to 15 angstroms were substantially the same as one another for each proteins. The RMSD drastically decreased as the cut-off distance increased from 5 to 10 angstroms. In the range of cut-off distance from 10 to 15 angstroms, the RMSD decreased slowly or reached at a plateau, and the RMSD values were small and close to the values for the structural alignments made by DDP with full structural environments.

When ΔN cut-off was not introduced, the RMSD decreased slowly after 15 angstroms, regardless of the kind of protein. However, when ΔN cut-off was introduced, the manner of variation in the RMSD greatly changed from protein to protein. For some proteins, the RMSD decreased slowly, exhibiting the same variation as in the case where ΔN cut-off was not introduced. For other proteins, the RMSD increased drastically.

Figure 17:
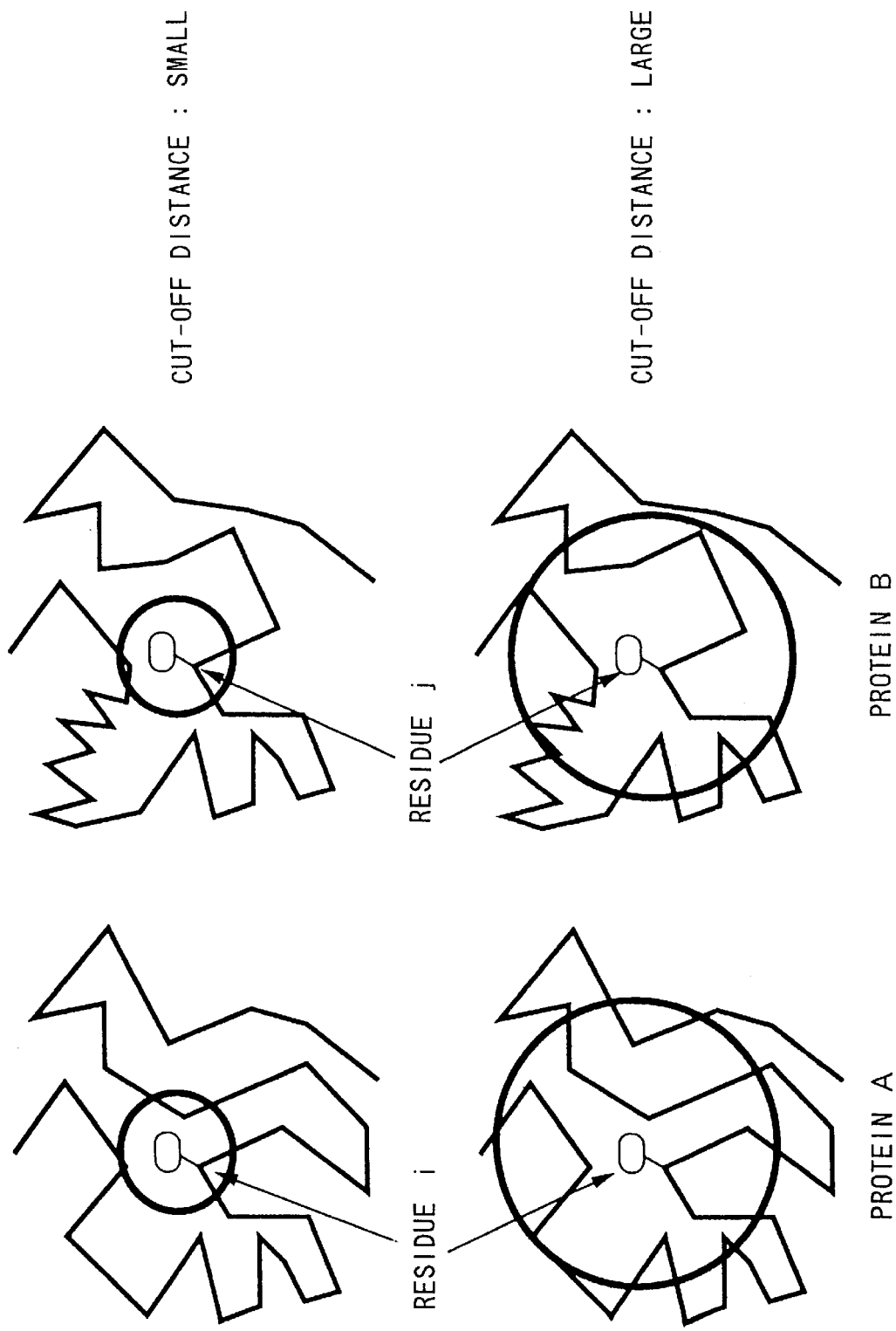
FIG. 17 is a diagram showing a case of small cut-off distance and a case of large cut-off distance.
Figure 18:
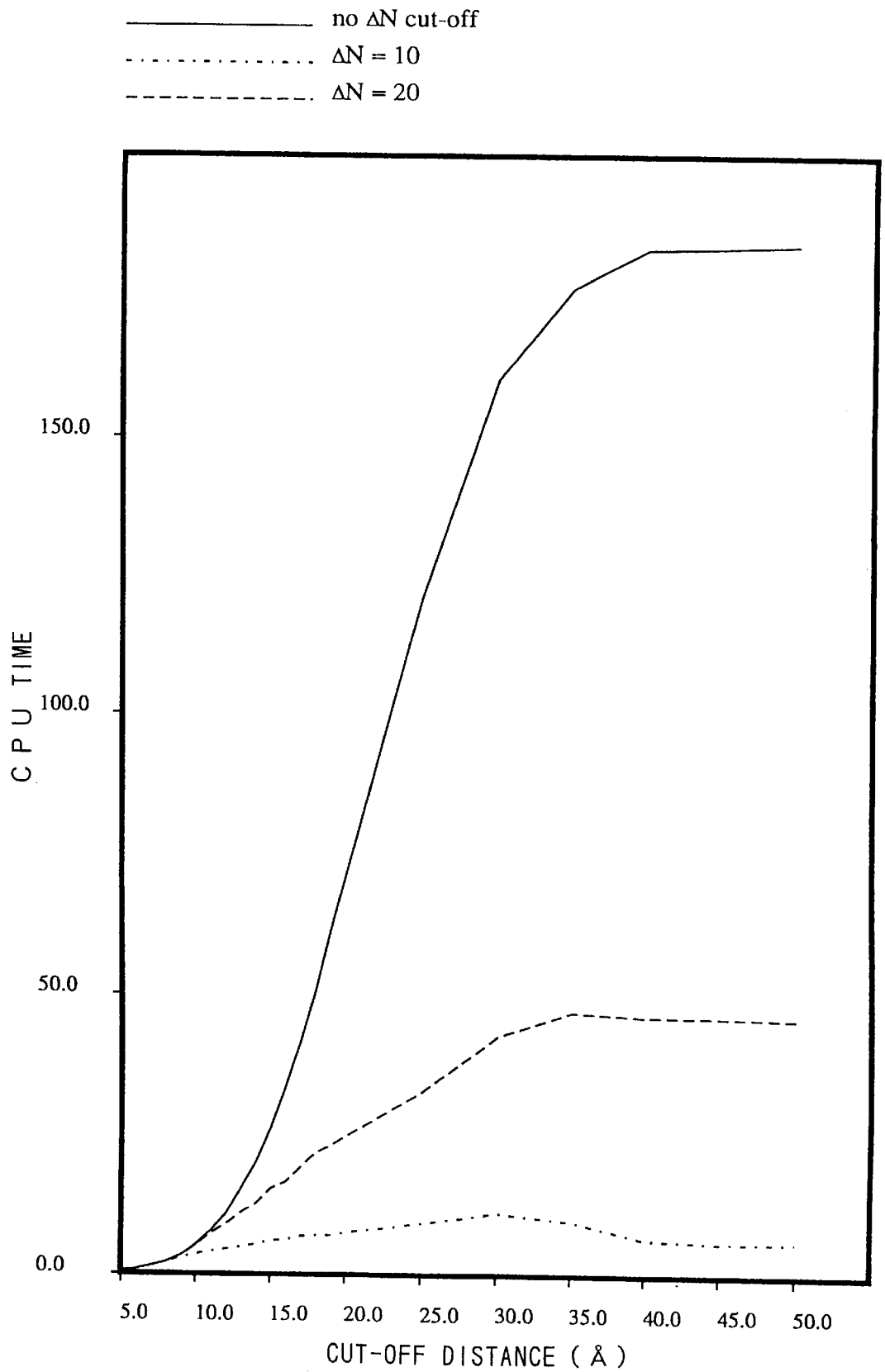
FIGS. 18–21 are plots each showing the relationship between cut-off distance and computational time.
Figure 19:
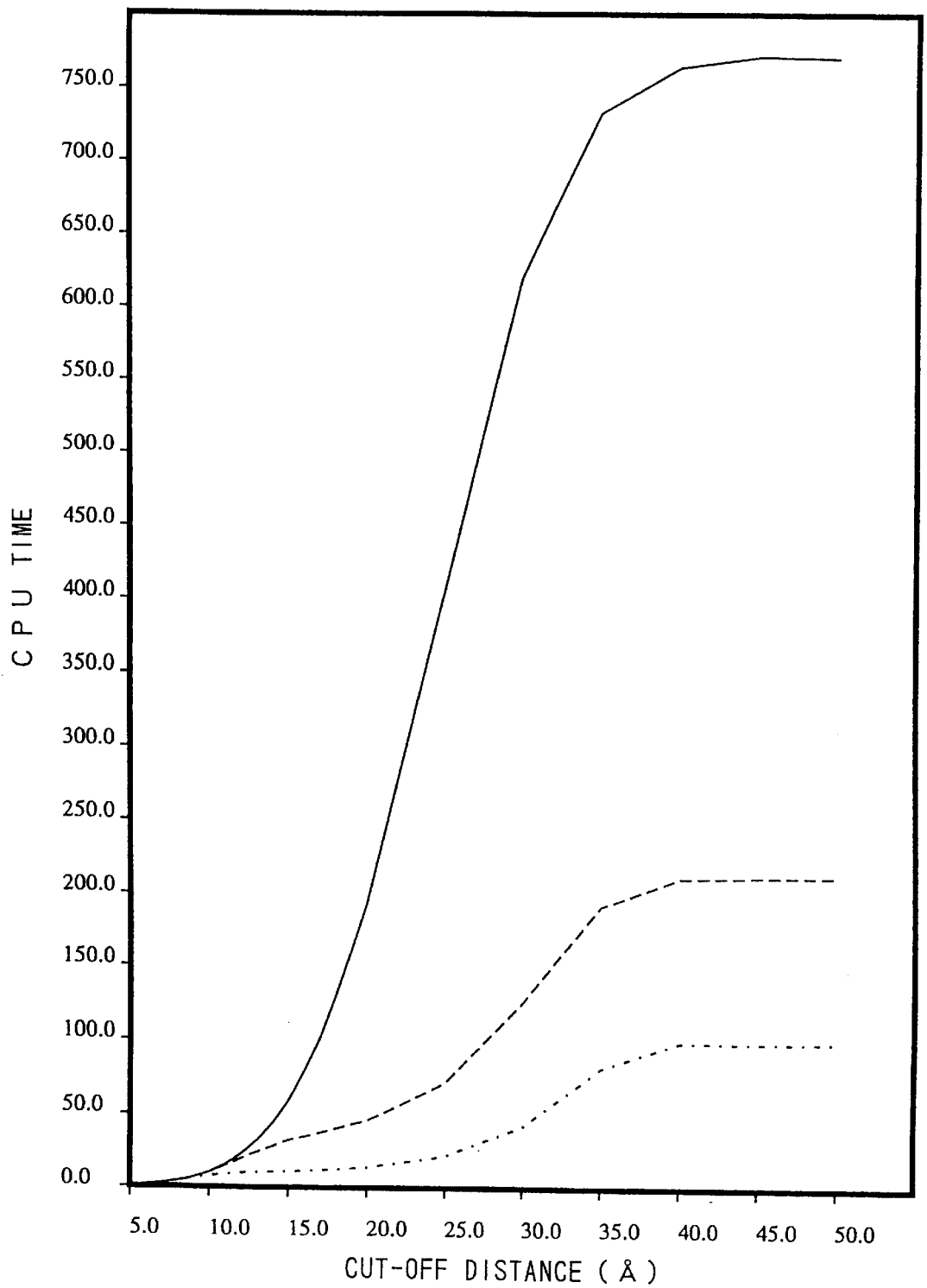
Figure 20:
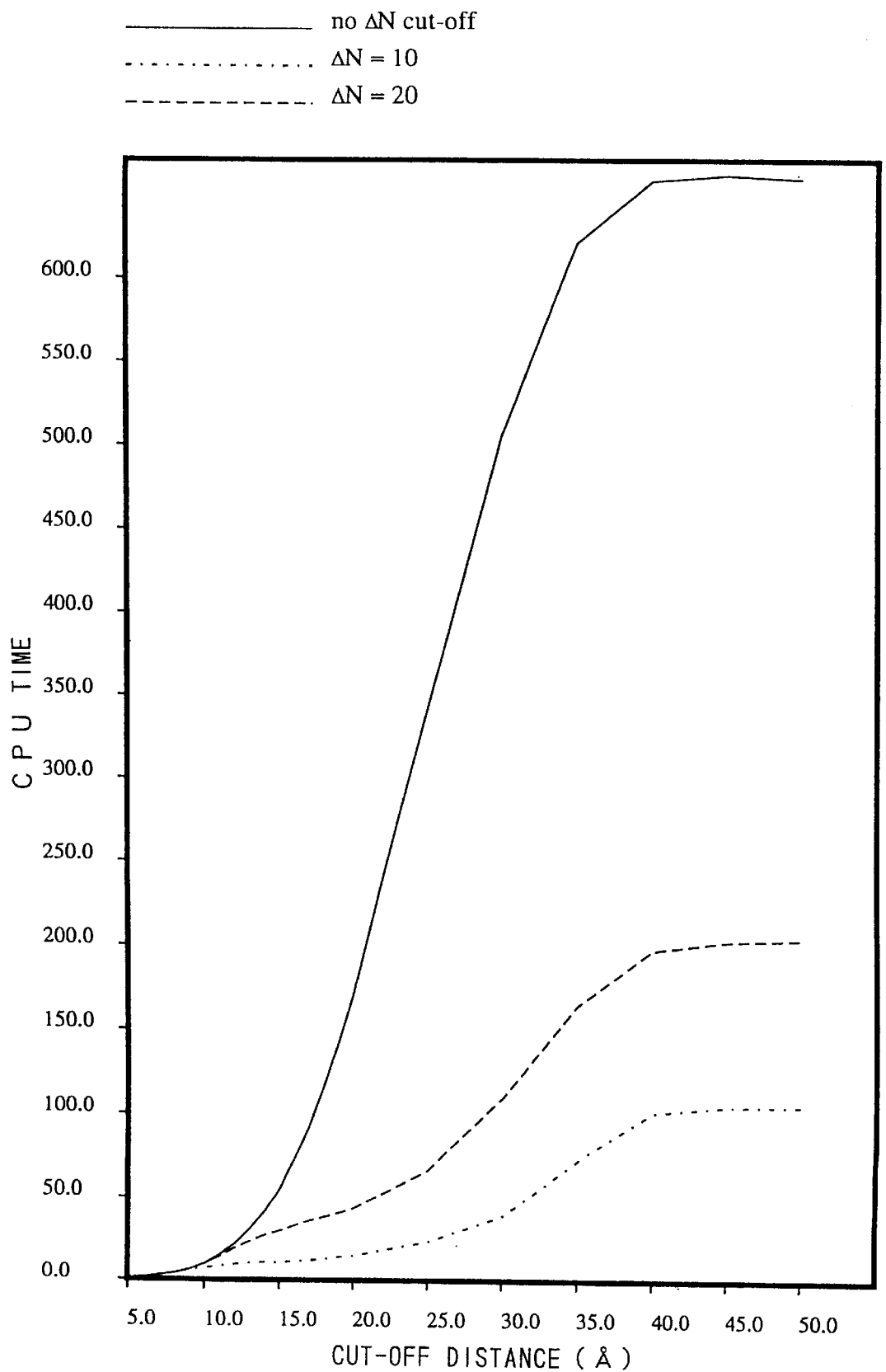
Figure 21:
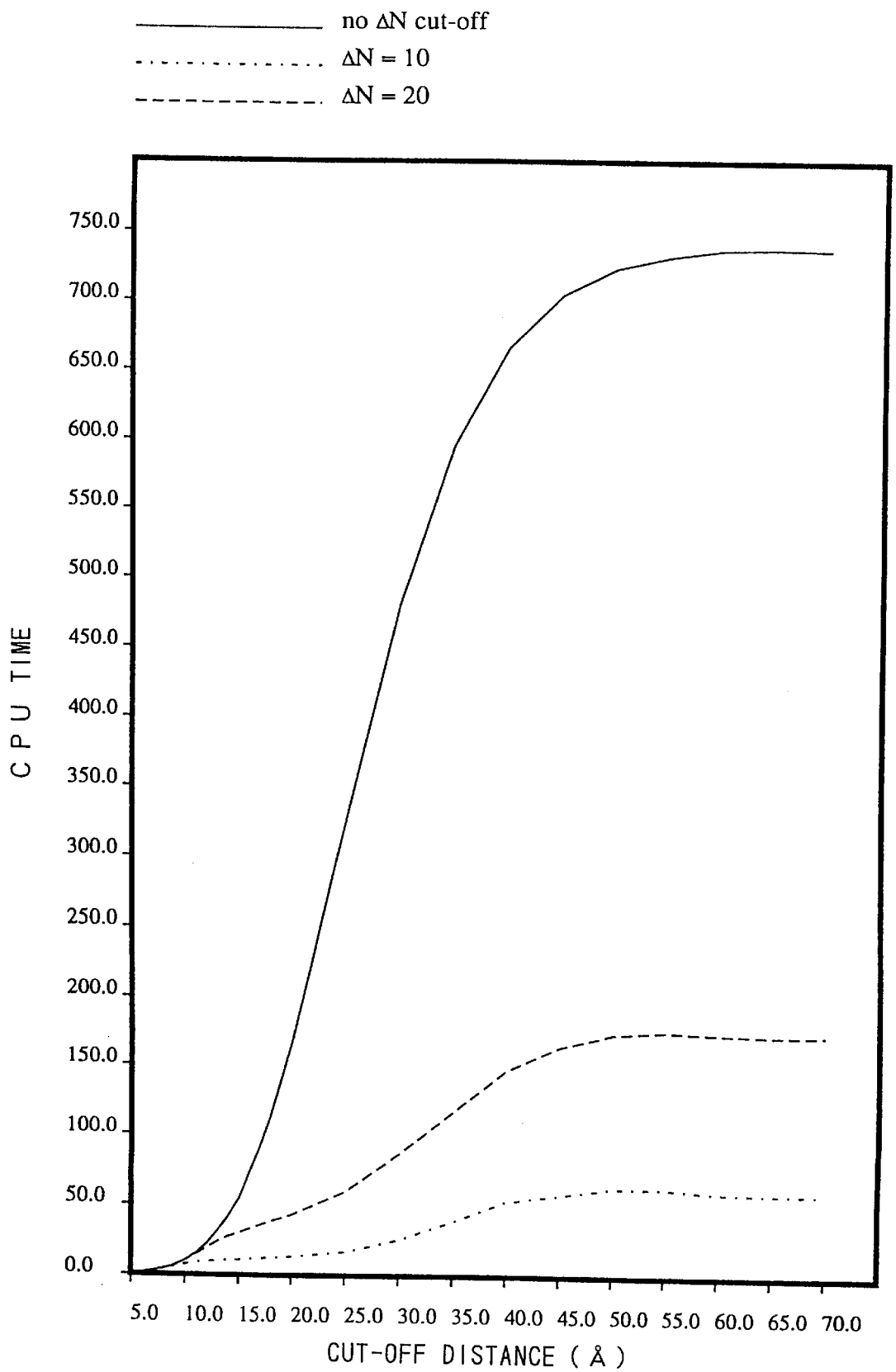

This phenomenon was considered to occur because of the following reason. When the cut-off distance is increased, many residues associated with insertion or deletion are included in the sphere. Then, due to ΔN cut-off, s(i,j) is not evaluated correctly even for structurally equivalent residues (see FIG. 17).

If the cut-off distance is restricted to be smaller than 10–15 angstroms, it is expected that such adverse effect will be suppressed, and high alignment accuracy will be achieved on average.

Such restriction is also supported from the viewpoint of computational time (FIGS. 18–21).

In each of these drawings, the vertical axis represents the processing time of a central processing unit (CPU time), while the horizontal axis represents the cut-off distance. As the cut-off distance increases, the CPU time increases. The introduction of ΔN cut-off reduces the CPU time. As the value of ΔN decreases, the CPU time increases. The cut-off distance corresponding to the rightmost ends of the lines is the same as that described above. Therefore, the vertical coordinate of the rightmost end of the solid line, which represents the case where ΔN cut-off is not introduced, corresponds to the CPU time in the case where the DDP algorithm is applied with the FSE. The comparison between the CPU times demonstrates that the introduction of the two approximations greatly reduces the computational time.

The results described above suggests that an alignment, which is satisfactory in terms of accuracy and computational time, is generated when the cut-off distance is set to a value within the range of 10–15 angstroms and ΔN is set to 10.

FIGS. 23–26 show alignments that were obtained for the four cases shown in Table 1 (FIG. 22) when the cut-off distance was set to 12 angstroms and ΔN was set to 10. FIG. 23 shows the alignment for Case 1 [β-protein 7fab1, 7fabh] (SEQ ID nos:3 and 4), FIG. 24 shows the alignment for Case 2 [β-protein 1mup, 1eph] (SEQ ID nos:5 and 6), FIG. 25 shows the alignment for Case 3 [α-protein 1mbc, 1gdi] (SEQ ID nos:7 and 8), and FIG. 26 shows the alignment for Case 4 [α-protein 1mbc, 1cpc] SEQ ID nos:9 and 10). Table 2 (FIG. 27) shows, for each of the four alignments, the CPU time, the RMSD, and the identity with respect to a corresponding alignment generated by DDP with FSE. For reference, the CPU time and the RSMD for the application of DDP with FSE are shown. There is no guarantee that the alignment generated by DDP with FSE is a correct structural alignment. However, the RMSD of such an alignment is generally small, and the secondary structure is properly aligned in many cases. Therefore, the alignment generated by DDP with FSE is here referred to as a correct answer. As shown in Table 2 (FIG. 27), the accuracy of the alignment decreased due to introduction of approximations, although the computational time was shortened.

(B) Effect of Two-step Alignment

When the DDP algorithm is applied only to selected residue pairs, the accuracy of a resultant alignment decreases. Therefore, Taylor and Orengo attempted to select 20 upper paths in terms of score and to apply the DDP algorithm to them again.

To follow their method, in the method of the present invention, the present inventors attempted to construct an alignment in two steps in order to prevent decrease in accuracy. Table 3 (FIG. 28) shows the results of alignment performed for the four cases listed in Table 1 (FIG. 22). The initial approximate alignment was obtained under the conditions that the cut-off distance was 12 angstroms and $\Delta N$ was 10. The value of $\Delta$ for defining a suboptimal region was $2\sigma$. Although the computational time increased slightly compared to the case of approximate computation, the obtained alignment had a close relationship with the alignment generated by DDP with FSE.

As is apparent from the above, the two methods are expected to be effective when they are selectively used in accordance with the purpose. The alignment with the two approximations is considered to be sufficient when computation speed is considered more important than accuracy (e.g., data base search, and construction of a guide tree for multiple alignment).

In contrast, when a strict residue-to-residue correspondence is required, a two-step alignment is advantageously used.

As described above, the DP algorithm has been expanded in various ways in the field of sequence analysis, and therefore the method of the present invention is expected to be improved to follow the expansion.

The above-described method of the present invention enables the structural alignment to be constructed in a shortened period of time in a simplified manner, while maintaining accuracy.

Next, the detail process of the method will be described with reference to FIGS. 29–31.

In FIG. 29, numeral 1 denotes an input section of inputting coordinate data of three-dimensional structures of two proteins; numeral 2 denotes a section to convert the coordinate data into the center-to-center distance between the side chains of a residue pair; numeral 3 denotes a section to construct a local environment through the distance cut-off approximation; numeral 4 denotes an upper-level DP matching section for residue alignment; numeral 5 denotes a section to determine the respective elements of a comparative matrix; and numeral 6 denotes a local environment comparison section. In the section 6, it is judged whether the $\Delta N$ cut-off condition is satisfied. When the $\Delta N$ cut-off condition is satisfied (YES), the local environment similarity is set to 0.0. When the $\Delta N$ cut-off condition is not satisfied (NO), the local environment similarity is calculated by the lower-level DP. Numeral 7 denotes a section to solve a recurrence equation for the lower-level DP, numeral 8 denotes a section to solve a recurrence equation for the upper-level DP, numeral 9 denotes a section to construct alignment by back tracking, and numeral 10 denotes an alignment output section.

The structural alignment by the double dynamic programming algorithm is performed in a sequence indicated by arrows. That is, coordinate data of three-dimensional structures of two proteins are input in the section 1, and the center-to-center distance between the side chains of a residue pair is obtained in the conversion section 2. In the section 3, a local environment is constructed through the distance cut-off approximation. To perform the upper-level DP in the section 4, the elements of the comparative matrix are determined in the section 5. In the section 5, local environments are compared in the section 6 at first. When the $\Delta N$ cut-off condition is satisfied (YES), the similarity in local environments is set to 0.0. When the $\Delta N$ cut-off condition is not satisfied (NO), the similarity in local environments is calculated by the lower-level DP. Subsequently, in the section 7, a recurrence equation for the lower-level DP is solved. Using the results of the comparison in the section 6, a recurrence equation is solved for the upper-level DP. Subsequently, in the section 9, an alignment is constituted by back tracking. Finally, the result of the alignment is output from the section 10.

Figure 30:
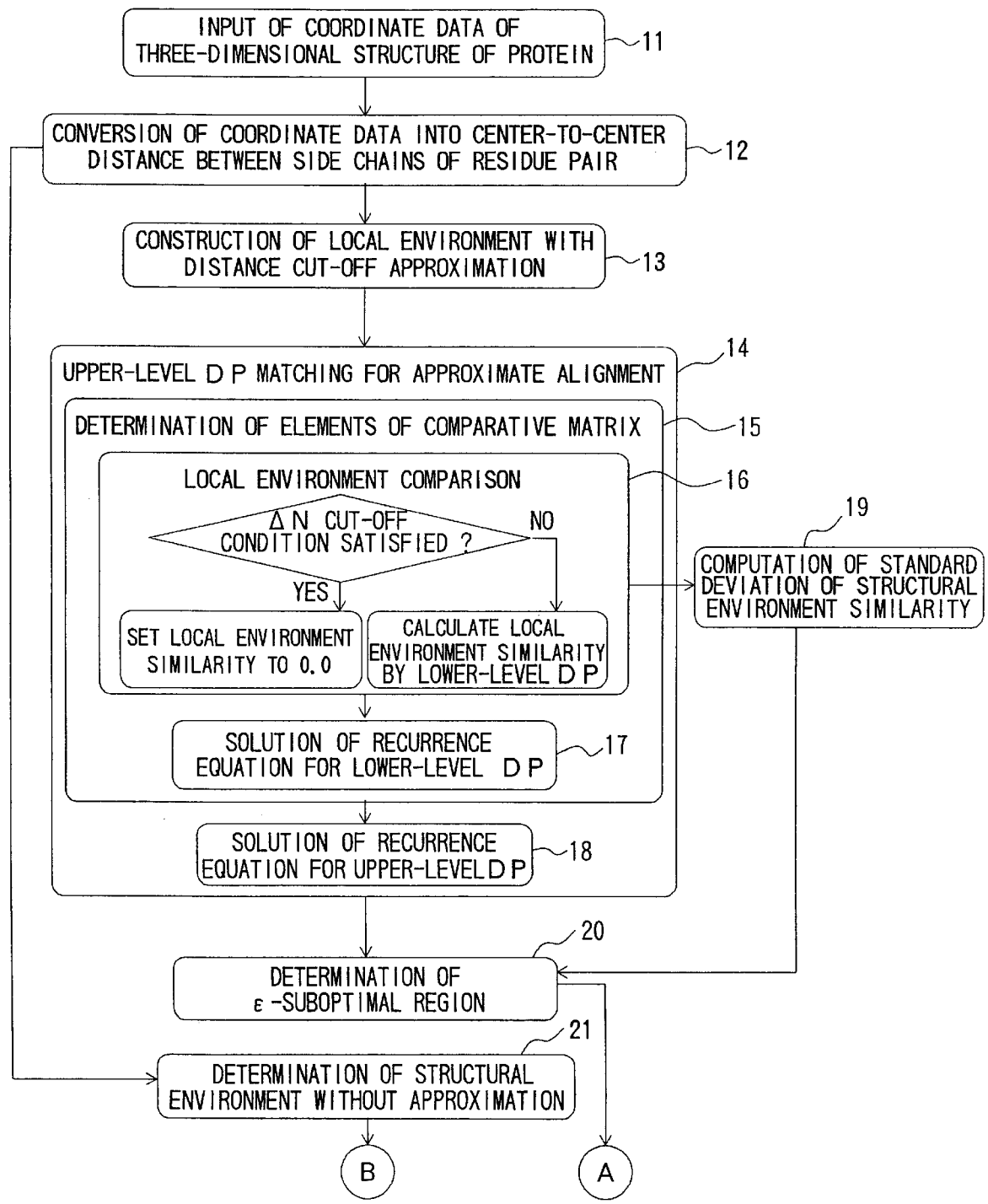
Figure 31:
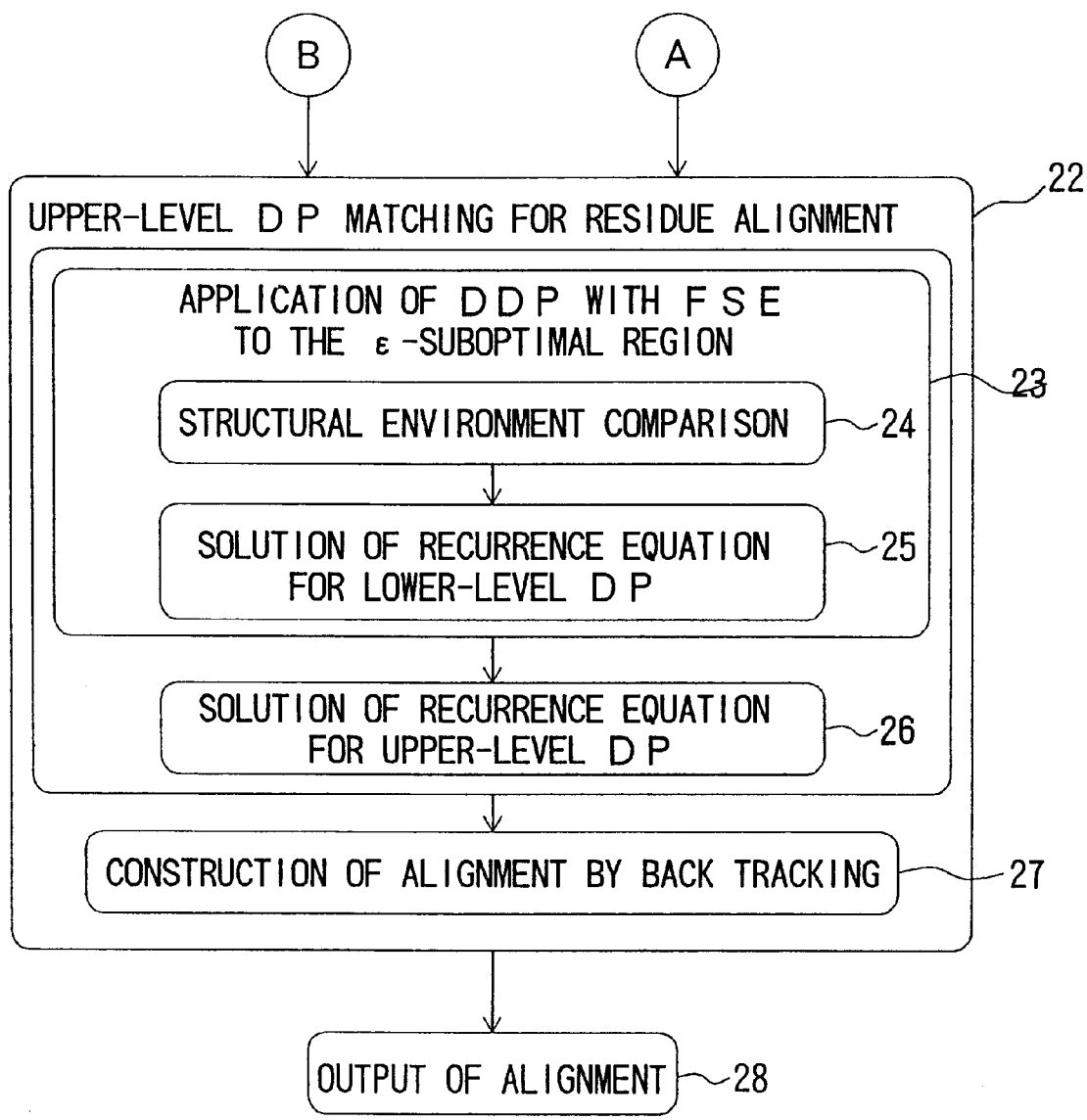

In FIGS. 30 and 31, numeral 11 denotes a section to input coordinate data of a three-dimensional structure of a protein; numeral 12 denotes a section to convert the coordinate data into the center-to-center distance between the side chains of a residue pair; numeral 13 denotes a section to construct a local environment through the distance cut-off approximation; numeral 14 denotes an upper-level DP matching section for approximate alignment; numeral 15 denotes a section to determine the respective elements of a comparative matrix; and numeral 16 denotes a local environment comparison section.

In the section 16, it is judged whether the $\Delta N$ cut-off condition is satisfied. When the $\Delta N$ cut-off condition is satisfied (YES), the local environment similarity is set to 0.0. When the $\Delta N$ cut-off condition is not satisfied (NO), the local environment similarity is calculated by the lower-level DP. Numeral 17 denotes a section for an application of a recurrence equation for the lower-level DP, and numeral 18 denotes a section for an application of a recurrence equation for the upper-level DP. Numeral 19 denotes a section to calculate a standard deviation of the structural environment similarity; numeral 20 denotes a section to determine the $\epsilon$-suboptimal region; numeral 21 denotes a section to determine the full structural environments; numeral 22 denotes a section to perform the upper-level DP; numeral 23 denotes a section to apply DDP calculation with FSE to the $\epsilon$-suboptimal region; numeral 24 denotes a section to compare structural environments; numeral 25 denotes a section to apply a recurrence equation for the lower-level DP, and numeral 26 denotes a section to solve a recurrence equation for the upper-level DP; numeral 27 denotes a section to construct an alignment by back tracking; and numeral 28 denotes an alignment output section.

This structural alignment by the double dynamic programming algorithm is performed in a sequence indicated by arrows. That is, coordinate data of a three-dimensional structure of a protein is input in the section 11, and the center-to-center distance between the side chains of a residue pair is obtained in the section 12. In the section 13, a local environment is constructed through the distance cut-off approximation.

After the completion of the processing in the section 12, the full structure environment is obtained in the section 21, which is then transferred to the section 22 for the upper-level DP.

The upper-level DP is performed in the section 14. At first, local environments are compared in the section 15. When the $\Delta N$ cut-off condition is satisfied (YES), the local environment similarity is set to 0.0. When the $\Delta N$ cut-off condition is not satisfied (NO), the local environment similarity is calculated by the lower-level DP. Subsequently, in the section 17, a recurrence equation for the lower-level DP is solved, and in section 18, a recurrence equation for the upper-level DP is solved. Subsequently, in the section 20, an ε-suboptimal region is determined.

---

What is claimed is:

1. A structural alignment method for proteins using a double dynamic programming algorithm, the method comprising the steps of:

(a) performing a first distance cut-off approximation for determining a first local environment of a first residue of a first protein centered at a side chain of said first residue of said first protein, and residues with side chain centers that are present within said first distance cut-off are selected as constituent elements of said first local environment of said first residue, wherein a number of residues in said first local environment is less than a number of residues in said first protein;

performing a second distance cut-off approximation for determining a second local environment of a second residue of a second protein centered at a side chain of said second residue of said second protein, and residues with side chain centers that are present within said second distance cut-off are selected as constituent elements of said second local environment of said second residue;

(b) performing $\Delta N$ cut-off approximation for selectively comparing residue pairs obtained by said first and second distance cut-off approximations having a first similarity of local environments, said first similarity having a value based on a result of said step of performing $\Delta N$ cut-off approximation;

(c) generating a 3-dimensional structural alignment of said first protein with said second protein using results of said first and second distance cut-off approximations and said $\Delta N$ cut-off approximation; and (d) outputting said 3-dimensional structural alignment indicating residue-to-residue correspondence between said first protein and said second protein, wherein said 3-dimensional structural alignment is generated so that a total sum of values of similarities for pairs of said first and second residues included in said 3-dimensional structural alignment is a maximum.

2. The method according to claim 1, wherein said step (a) further comprises the step of selecting a first plurality of first local environment residues, each one of said first plurality of first local environment residues having a side chain center located within a sphere, said sphere having a predetermined radius and a sphere center at said side chain of said first residue, wherein said first local environment includes said first plurality of first local environment residues.

3. The method according to claim 2, wherein said radius is 10 to 15 angstroms, and $\Delta N$ is 10.

4. The method according to claim 2, further comprising the step of performing said double dynamic programming algorithm for a plurality of residue pairs within an $\epsilon$-suboptimal region which is determined based on results of said step (a) and said step (b), wherein said step of performing said double dynamic programming algorithm is performed without repeating said distance cut-off approximation and said $\Delta N$ cut-off approximation.

5. The method according to claim 1, wherein a second similarity of local environments is one of set to have a value of 0.0 by said $\Delta N$ cut-off, or calculated by a lower level dynamic programming algorithm.

6. The method according to claim 1, wherein said first local environment includes a plurality of first environment residues, and said second local environment includes a plurality of second environment residues; and said method further includes:

selecting a first group of said first environment residues and determining a number of said first environment residues selected;

selecting a second group of said second environment residues and determining a number of said second environment residues selected; and comparing said number of selected first environment residues with said number of selected second environment residues.

7. The method according to claim 1, wherein said first local environment includes a plurality of first environment residues, and said second local environment includes a plurality of second environment residues; and said method further includes:

dividing said first environment residues into a first group and a second group based on locations of said first environment residues with respect to said first residue, and determining a number of said first environment residues in said first group and a number of said first environment residues in said second group;

dividing said second environment residues into a third group and a fourth group based on locations of said second environment residues with respect to said second residue and determining a number of said second environment residues in said third group and determining a number of said second environment residues in said fourth group; and comparing said number of said first environment residues in said first group with said number of said second environment residues in said third group.

8. The method according to claim 7, wherein said first group is located on an N-terminal side of said first protein with respect to said first residue;

said second group is located on a C-terminal side of said first protein with respect to said first residue;

said third group is located on an N-terminal side of said second protein with respect to said second residue;

said fourth group is located on a C-terminal side of said second protein with respect to said second residue.

9. The method according to claim 7, further comprising determining whether at least one of a first difference between said number of first environment residues of said first group and said number of second environment residues of said third group is at least as large as a predetermined first threshold value, and a second difference between said number of residues of said second group and said number of residues of said fourth group is at least as large as a predetermined second threshold value.

10. The method according to claim 7, further comprising determining said first similarity by comparing a difference between said number of residues of said first group and said number of residues of said third group with a predetermined third threshold value and comparing a difference between said number of residues of said second group and said number of residues of said fourth group with a predetermined fourth threshold value.

11. The method according to claim 1, further comprising constructing a first alignment using said distance cut-off approximation and said ΔN cut-off approximation; and constructing a second alignment by determining an ε-suboptimal region for said first alignment.

12. The method according to claim 11, further comprising performing said double dynamic programming algorithm for a plurality of residue pairs within said ε-suboptimal region.

13. A computer-implemented system for structural alignment of proteins using a double dynamic programming algorithm, the system comprising:

means for performing a first distance cut-off approximation for determining a first local environment of a first residue of a first protein centered at a side chain of said first residue of said first protein, and residues with side chain centers that are present within said first distance cut-off are selected as constituent elements of said first local environment of said first residue, wherein a number of residues in said first local environment is less than a number of residues in said first protein;

means for performing a second distance cut-off approximation for determining a second local environment of a second residue of a second protein centered at a side chain of said second residue of said second protein, and residues with side chain centers that are present within said second distance cut-off are selected as constituent elements of said second local environment of the second residue;

means for performing ΔN cut-off approximation for selectively comparing residue pairs obtained by said first and second distance cut-off approximations having a similarity of local environments, said similarity having a value based on a result of performing said ΔN cut-off approximation; and means for generating a 3-dimensional structural alignment of said first protein with said second protein using results of said first and second distance cut-off approximations and said ΔN cut-off approximation; and means for outputting said 3-dimensional structural alignment, said 3-dimensional structural alignment indicating residue-to-residue correspondence between said first protein and said second protein, wherein said 3-dimensional structural alignment is generated so that a total sum of values of similarities for pairs of said first and second residues included in said 3-dimensional structural alignment is a maximum.

14. The system according to claim 13, wherein said means for performing said first distance cut-off approximation further comprises means for selecting a plurality of first local environment residues, each one of said plurality of first local environment residues having a side chain center located within a sphere, said sphere having a predetermined radius and a sphere center at said side chain of said first residue, wherein said first local environment includes said plurality of first local environment residues.

15. The system according to claim 14, wherein said means for generating comprises:

means for determining an ε-suboptimal region which includes a plurality of residue pairs, said ε-suboptimal region determined as a result of said distance cut-off and said ΔN cut-off, and means for performing said double dynamic programming algorithm for said plurality of residue pairs within said ε-suboptimal region, without repeating said distance cut-off approximation and said ΔN cut-off approximation.

16. The system according to claim 15, wherein said radius is 10 to 15 angstroms, and ΔN is 10.

17. A computer program product including a computer readable medium, the computer readable medium embodying a program of instructions executable by a computer to perform method steps for structural alignment of proteins using a double dynamic programming algorithm, the method steps comprising:

performing a first distance cut-off approximation for determining a first local environment of a first residue of a first protein centered at a side chain of said first residue of said first protein, and residues with side chain centers that are present within said first distance cut-off are selected as constituent elements of said first local environment of said first residue, wherein a number of residues in said first local environment is less than a number of residues in said first protein;

performing a second distance cut-off approximation for determining a second local environment of a second residue of a second protein centered at a side chain of said second residue of said second protein, and residues with side chain centers that are present within said second distance cut-off are selected as constituent elements of said second local environment of said second residue;

performing $\Delta N$ cut-off approximation for selectively comparing residue pairs obtained by said first and second distance cut-off approximations having a similarity of environments, said similarity having a value based on a result of said step of performing $\Delta N$ cut-off approximation;

generating a 3-dimensional structural alignment of said first protein with said second protein using results of said first and second distance cut-off approximations and said $\Delta N$ cut-off approximation; and outputting said 3-dimensional structural alignment indicating residue-to-residue correspondence between said first protein and said second protein, wherein said 3-dimensional structural alignment is generated so that a total sum of values of similarities for pairs of said first and second residues included in said 3-dimensional structural alignment is a maximum.

18. The computer program product according to claim 17, wherein said step of performing a first distance cut-off approximation further comprises selecting a plurality of first local environment residues, each one of said plurality of first local environment residues having a side chain center located within a sphere, said sphere having a predetermined radius and a sphere center at said side chain of said first residue, wherein said first local environment includes said plurality of first local environment residues.

19. The computer program product according to claim 18, wherein said method step of generating comprises:

determining an $\epsilon$-suboptimal region which includes a plurality of residue pairs, said $\epsilon$-suboptimal region determined based on results of said performing said first and second distance cut-off approximations and said performing said $\Delta N$ cut-off approximation, and performing said double dynamic programming algorithm for said plurality of residue pairs within said $\epsilon$-suboptimal region, without repeating said distance cut-off approximation and said $\Delta N$ cut-off approximation.

20. The computer program product according to claim 18, wherein said radius is 10 to 15 angstroms, and $\Delta N$ is 10.

* * * * *